(12) United States Patent
Prasad et al.

(10) Patent No.: US 11,544,848 B2
(45) Date of Patent: Jan. 3, 2023

(54) DEEP LEARNING BASED METHODS AND SYSTEMS FOR AUTOMATED SUBJECT ANATOMY AND ORIENTATION IDENTIFICATION

(71) Applicant: GE Precision Healthcare LLC, Wauwatosa, WI (US)

(72) Inventors: Raghu Prasad, Bangalore (IN); Harikrishna Rai, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 203 days.

(21) Appl. No.: 17/091,179

(22) Filed: Nov. 6, 2020

(65) Prior Publication Data

US 2022/0148157 A1 May 12, 2022

(51) Int. Cl.
*G06T 7/00* (2017.01)
*G16H 30/20* (2018.01)
*G06N 20/00* (2019.01)

(52) U.S. Cl.
CPC .......... *G06T 7/0012* (2013.01); *G06N 20/00* (2019.01); *G16H 30/20* (2018.01);
(Continued)

(58) Field of Classification Search
CPC ......... G06T 7/0012; G06T 2207/10028; G06T 2207/10088; G06T 2207/20081;
(Continued)

(56) References Cited

U.S. PATENT DOCUMENTS 6,049,281 A 4/2000 Osterweil
10,456,102 B2 10/2019 Don
(Continued)

FOREIGN PATENT DOCUMENTS

EP 3646794 A1 5/2020

OTHER PUBLICATIONS

Little et al., "Unified Database for Rejected Image Analysis Across Multiple Vendors in Radiography," Journal of the American College of Radiology 14.2 (2017); 208-216, 9 pages.

*Primary Examiner* — Van D Huynh

(57) ABSTRACT

Systems and methods for automated patient anatomy and orientation identification using an artificial intelligence (AI) based deep learning module are provided. The method comprises positioning a subject over a table of a magnetic resonance imaging (MRI) system and wrapping at least one radiofrequency (RF) imaging coil over the subject. The method comprises obtaining a plurality of depth images, color images and infrared images of the subject using a three-dimensional (3D) depth camera and identifying the table boundary of the MRI system using the images obtained by the 3D camera. The method further comprises identifying a location of the subject over the table to determine if the subject is positioned within the table boundary of the MRI system and identifying a plurality of key anatomical points or regions corresponding to a plurality of organs of the subject body. The method further comprises identifying all DICOM orientations of the subject over the table of the MRI system and identifying the coils of the MRI system wrapped around the subject body and determining the orientation of the subject with respect to the coils of the MRI system, hospital gown, and blankets. The method further comprises identifying the anatomical key points occluded by the coils of the MRI system, hospital gown, and blankets to determine accurate positioning of the coils of the MRI system over the subject anatomy for automated landmarking of anatomies and imaging.

23 Claims, 19 Drawing Sheets

(52) U.S. Cl.
CPC ............... *G06T 2207/10028* (2013.01); *G06T 2207/10088* (2013.01); *G06T 2207/20081* (2013.01); *G06T 2207/20084* (2013.01)

(58) Field of Classification Search
CPC .......... G06T 2207/20084; G06N 20/00; G16H 30/20; G16H 30/40; G16H 40/63; G16H 50/20
USPC ........................................................ 382/128
See application file for complete search history.

(56) References Cited

U.S. PATENT DOCUMENTS

| | | | |
|---|---|---|---|
| 2002/0065461 A1* | 5/2002 | Cosman | G06T 7/73 600/429 |
| 2009/0149737 A1* | 6/2009 | Hansen | G01R 33/36 324/322 |
| 2012/0206140 A1* | 8/2012 | Banerjee | G01R 33/56509 324/309 |
| 2013/0060129 A1* | 3/2013 | Lee | G01R 33/543 600/415 |
| 2017/0184692 A1* | 6/2017 | Gu | G01R 33/341 |
| 2019/0318497 A1* | 10/2019 | Zhao | A61B 6/0407 |
| 2020/0058106 A1* | 2/2020 | Lazarus | G06V 10/774 |
| 2020/0294287 A1* | 9/2020 | Schlemper | G01R 33/36 |
| 2020/0309880 A1* | 10/2020 | Bi | G01R 33/307 |
| 2021/0080531 A1* | 3/2021 | Gui | G06N 3/084 |

* cited by examiner

DEEP LEARNING BASED METHODS AND SYSTEMS FOR AUTOMATED SUBJECT ANATOMY AND ORIENTATION IDENTIFICATION

FIELD OF THE INVENTION

This disclosure relates generally to improved medical imaging systems and methods, and more particularly to systems and methods for automated patient anatomy and orientation identification using an artificial intelligence (AI) based deep learning module during occlusion from the coils of a magnetic resonance imaging (MRI) system using a three-dimensional (3D) depth camera.

BACKGROUND OF THE INVENTION

Various medical imaging systems and methods are used to obtain the images of the affected regions of the subject anatomy for diagnosing the medical conditions. Magnetic resonance imaging (MRI) is a known medical imaging technique used for imaging the different body parts like head, chest, abdomen and legs of a subject. MR imaging involves positioning the subject on a table of the patient positioning system of the MRI device and moving the patient positioning system inside the gantry of the MRI device for imaging. The MRI systems may contain a variety of imaging radiofrequency (RF) coils, for example a whole-body radiofrequency coil may be adapted to transmit the waveform towards the subject and configured to receive the waves from the subject to acquire the image data from the subject.

Although the images produced by the MR imaging techniques are of good quality, many images are adversely affected by the operational conditions of the MRI system and the subject movement. Movement of the subject, wrong positioning of the subject on patient positioning system, wrong positioning of the imaging coil over the subject may result in faulty images being obtained by the MRI system. Such images might be rejected by the radiologist and reimaging of the subject becomes necessary for obtaining the high-quality user viewable images. Precious time for treating the subject in serious medical conditions like trauma may be lost due to such imaging errors resulting in worsening the subject health conditions. Therefore, to avoid rejection of the MR images, it is very critical to accurately implement the imaging technique.

A skilled operator is required for accurate imaging of the subject using the MRI devices. Any error on part of the operator would result in an image containing an excessive disturbance or noise. Therefore, training of the operator and her experience in handling the MR imaging devices will affect the MR image quality. The operator may be skilled in acquiring the good quality images of the certain portion of the body due to her experience in obtaining the images of that body portion, but the operator may not be skilled to obtain the high-quality images of the entire subject body. This may be due to the lack of the imaging experience or lack of the anatomical knowledge of the entire body. Also, placing the MR imaging coils at the appropriate body portion affects the quality of the image. Physical parameters of the subject body like obesity, bone density, height, chest or abdominal size will create a challenging situation for the operator to correctly position the MR imaging coil for obtaining the complete image of the region of interest. Any wrong placement of the MR imaging coil would result in poor image quality and rejection of images of the regions of interest.

A study conducted by Little, Kevin J. et al. titled "Unified database for rejected images analysis across multiple vendors in radiography" in the Journal of the American college of Radiology 14.2 (2017); 208-2016 cites major reasons of the image rejection. These rejection reasons may include an incorrect positioning of the subject over the patient positioning system, incorrect use of the imaging technique by the operator, movement of the subject, imaging artifacts and others. The study further indicates that amongst the rejected images for different body organs and systems, the rejection percentage of the images of the chest, abdomen, pelvis and spine region was higher than the other body organs.

Majority of the pre-scan errors in the MRI radiological workflows are due to in-appropriate positioning of the subject, incorrect imaging protocol followed by the operator of the MRI system for the anatomy to be scanned and negligence of the operator/technologist. The operator/technologist who is responsible for scanning the subject may commit pre-scan errors such as scanning the subject with incorrect subject orientation, scanning the subject with inappropriate pose, angle, and direction. Further, when the subject checks-in the scanner room with a prescription of the body part to be scanned, the operator reviews the prescription, and then prepares the patient for the scan. During this process, pre-scan errors may be committed due to for example the operator mis-interpreting the prescription and instructing the subject towards an in-appropriate pose and orientation. The subject may mis-interpret the instructions given by the operator, leading to an inappropriate pose and orientation. In another example, the operator may not pay attention to incorrect pose and orientation of the subject and completes the scan.

All these pre-scan errors may lead to rejection and repetition of the scans. This causes discomfort to the subject, increases the subject wait time and the cognitive stress on the operator and the radiologists, and further reduces the throughput of the scanner machine. Further, the operator/radiologist must manually select the appropriate imaging protocol for scanning the subject based on the positioning and orientation/pose. This is always error prone, because if the operator/technologist is not alert enough to pull the correct protocol, they end up scanning the patient with a wrong protocol or an incorrect posture.

Therefore, systems and methods are required for providing an automated guidance to the scanning personnel to appropriately position the subject on the table of the MRI system, set the scan parameters, use the appropriate imaging coils of the MRI system and scan the regions of the subject to generate the high quality MR images with minimum errors.

SUMMARY OF THE INVENTION

This summary introduces concepts that are described in more detail in the detailed description. It should not be used to identify essential features of the claimed subject matter, nor to limit the scope of the claimed subject matter. Its sole purpose is to present concepts in a simplified form as a prelude to the more detailed description that is presented later.

In accordance with an aspect of the disclosure a method is disclosed for automated anatomy and orientation identification of a subject using an artificial intelligence (AI) based deep learning module. The method comprises positioning a subject over a table of a magnetic resonance imaging (MRI) system and wrapping at least one radiofrequency (RF) imaging coil over the subject. The method further comprises obtaining a plurality of depth images, color images and infrared images of the subject using a three-dimensional (3D) depth camera. The method further comprises identifying a table boundary of the MRI system using the images obtained by the 3D camera. The method further comprises identifying a location of the subject over the table to determine if the subject is positioned within the table boundary of the MRI system and identifying a plurality of key anatomical points corresponding to a plurality of organs of the subject body. The method further comprises identifying an orientation of the subject over the table of the MRI system. The method further comprises identifying the coils of the MRI system wrapped around the subject body and determining the orientation of the subject with respect to the coils of the MRI system. The method further comprises identifying the anatomical key points occluded by the coils of the MRI system to determine accurate positioning of the coils of the MRI system over the subject anatomy for imaging.

In accordance with an aspect of the disclosure a system is disclosed for automated anatomy and orientation identification of a subject using an artificial intelligence (AI) based deep learning module during occlusion from an imaging coil of a magnetic resonance imaging (MRI) system. The system comprises a three-dimensional (3D) depth camera configured to capture a plurality of depth images, color images and infrared images of a subject positioned on a table of the magnetic resonance imaging (MRI) system. The system further comprises a computer system connected to the 3D depth camera and configured to receive the plurality of images from the 3D depth camera. The computer system comprises a processor; a memory connected to the processor and at least one artificial intelligence (AI) based deep learning module deployed over the memory. The AI based deep learning module may be configured to identify a table boundary of the MRI system using the images obtained by the 3D camera. The AI based deep learning module may be further configured to identify a location of the subject over the table to determine if the subject is positioned within the table boundary of the MRI system and identify a plurality of key anatomical points corresponding to a plurality of organs of the subject body. The AI based deep learning module may be further configured to identify an orientation of the subject over the table of the MRI system and identify the MRI coils wrapped around the subject body and determine the orientation of the subject with respect to the MRI coils. The AI based deep learning module may be further configured to identify the anatomical key points occluded by the MRI coils to determine an accurate position of the MRI coil over the subject anatomy for imaging.

DETAILED DESCRIPTION

Figure 1A:
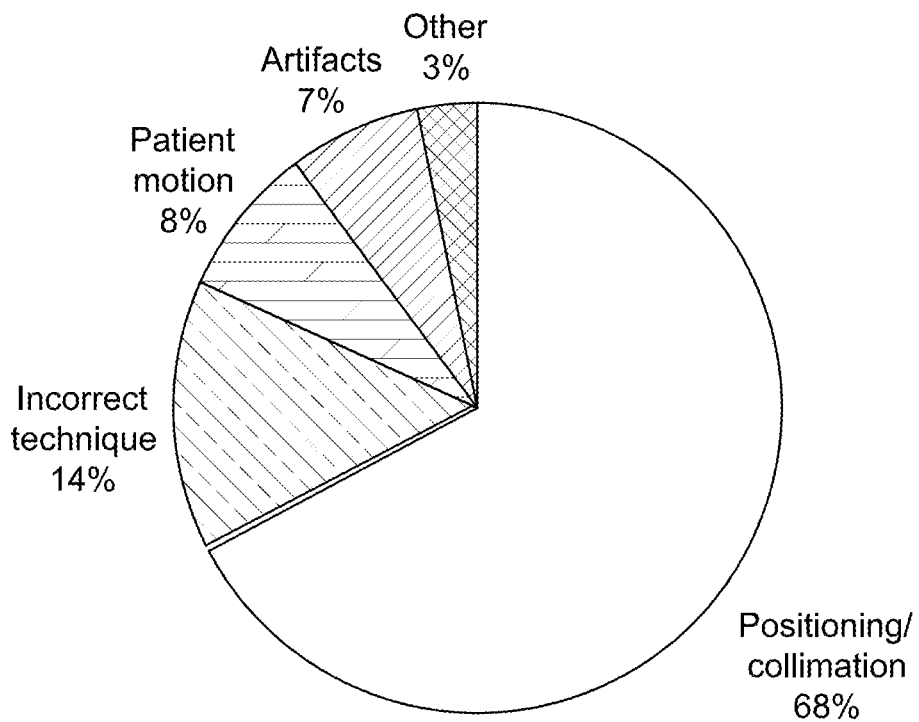
FIG. 1(a) is a graphical representation of the various operational parameters responsible for rejection of the MR images according to an aspect of the disclosure.

In the following specification and the claims, reference will be made to a few terms, which shall be defined to have the following meanings.

The singular forms "a", "an", and "the" include plural references unless the context clearly dictates otherwise.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the terms "software" and "firmware" are interchangeable and include any computer program stored in memory for execution by devices that include, without limitation, mobile devices, clusters, personal computers, workstations, clients, and servers.

As used herein, the term "computer" and related terms, e.g., "computing device", "computer system" "processor", "controller" are not limited to integrated circuits referred to in the art as a computer, but broadly refers to at least one microcontroller, microcomputer, programmable logic controller (PLC), application specific integrated circuit, and other programmable circuits, and these terms are used interchangeably herein.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

In one aspect of the disclosure a method is disclosed for automated anatomy and orientation identification of a subject using an artificial intelligence (AI) based deep learning module. The method comprises positioning a subject over a table of a magnetic resonance imaging (MRI) system and wrapping at least one radiofrequency (RF) imaging coil over the subject. The method further comprises obtaining a plurality of depth images, color images and infrared images of the subject using a three-dimensional (3D) depth camera.

The method further comprises identifying a table boundary of the MRI system using the images obtained by the 3D camera. The method further comprises identifying a location of the subject over the table to determine if the subject is positioned within the table boundary of the MRI system and identifying a plurality of key anatomical points corresponding to a plurality of organs of the subject body. The method further comprises identifying an orientation of the subject over the table of the MRI system. The method further comprises identifying the coils of the MRI system wrapped around the subject body and determining the orientation of the subject with respect to the coils of the MRI system. The method further comprises identifying the anatomical key points occluded by the coils of the MRI system to determine accurate positioning of the coils of the MRI system over the subject anatomy for imaging.

In another aspect of the disclosure a system is disclosed for automated anatomy and orientation identification of a subject using an artificial intelligence (AI) based deep learning module during occlusion from an imaging coil of a magnetic resonance imaging (MRI) system. The system comprises a three-dimensional (3D) depth camera configured to capture a plurality of depth images, color images and infrared images of a subject positioned on a table of the magnetic resonance imaging (MRI) system. The system further comprises a computer system connected to the 3D depth camera and configured to receive the plurality of images from the 3D depth camera. The computer system comprises a processor; a memory connected to the processor and at least one artificial intelligence (AI) based deep learning module deployed over the memory. The AI based deep learning module may be configured to identify a table boundary of the MRI system using the images obtained by the 3D camera. The AI based deep learning module may be further configured to identify a location of the subject over the table to determine if the subject is positioned within the table boundary of the MRI system and identify a plurality of key anatomical points corresponding to a plurality of organs of the subject body. The AI based deep learning module may be further configured to identify an orientation of the subject over the table of the MRI system and identify the MRI coils wrapped around the subject body and determine the orientation of the subject with respect to the MRI coils. The AI based deep learning module may be further configured to identify the anatomical key points occluded by the MRI coils to determine an accurate position of the MRI coil over the subject anatomy for imaging.

Embodiments of the present disclosure will now be described, by way of example, with reference to the figures, in which FIG. 1 shows a graphical representation of the various operational parameters responsible for rejection of the MR images according to an aspect of the disclosure. Magnetic resonance (MR) imaging involves positioning the subject on the table of the MRI system and moving the table inside the gantry of the MRI system for imaging. The subject may be positioned and oriented on the table in various imaging positions based on the imaging requirements. Some of the examples of patient positions on the table include head-first, feet first, supine prone, left decubitus and right decubitus. Positioning and orientation of the subject on the table of the MRI system may be influenced by the region or the organs of the subject to be imaged. In one example, the subject may be placed in "head first" and "supine" position on the table for imaging the lungs within the chest portion of the subject and an imaging coil of the MRI system may be positioned on the chest for acquiring the image data from the subject body. Such positioning of the imaging coils on different portions of the subject body to be imaged is prone to several errors. FIG. 1(a) shows the classification of all such imaging errors that may result in rejection of the MR images. It may be seen that inaccurate positioning of the subject over the table is one of the most important reason for generating inaccurate MR images and resulting in rejection of the images. Other prominent reasons for inaccurate MR images include incorrect imaging protocol being followed by the operator of the MR imaging system, motion of the patient or the patient organs during imaging for example, movement of the subject arms, hands or legs. These rejections of the MR images are highly influenced by the accuracy with which the operator follows the imaging protocol and always subject to human error.

Figure 1B:
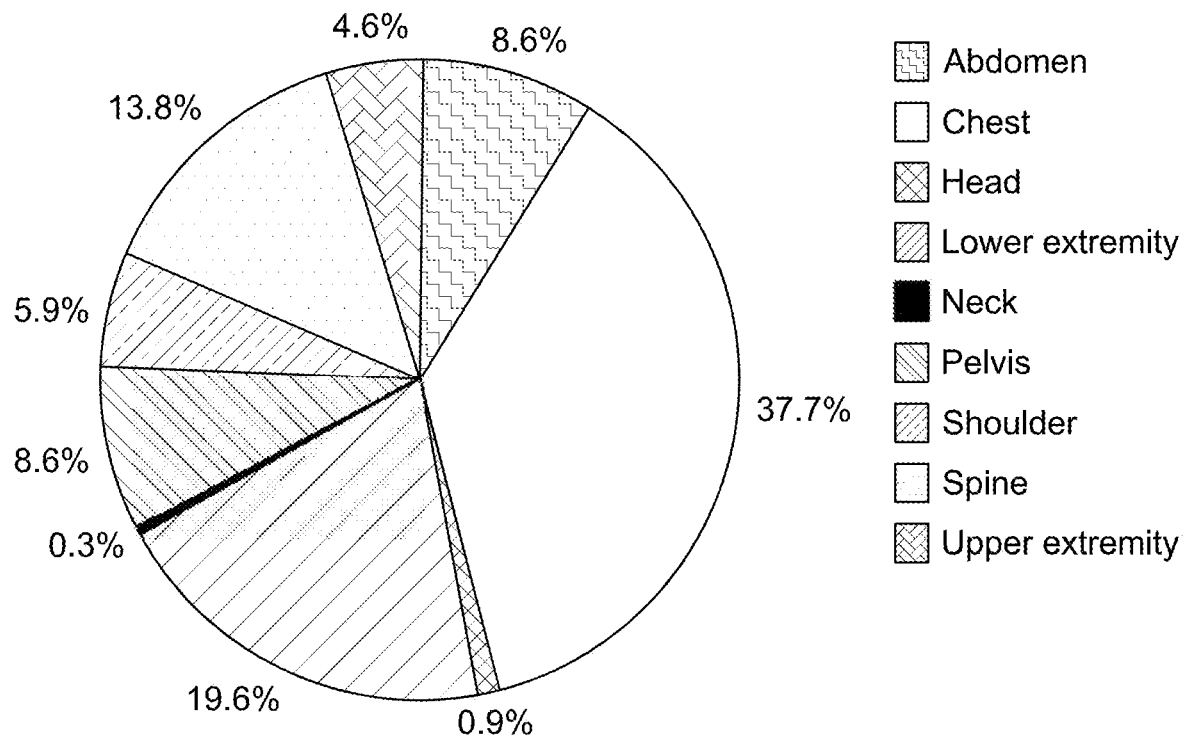
FIG. 1(b) illustrates a pie chart representing organ-wise distribution of the rejected MR images according to an aspect of the disclosure.

In accordance with an aspect of the disclosure, FIG. 1(b) shows a pie chart representing organ-wise distribution of the rejected MR images. Rejection of the MR images is more frequent for certain organs than the other. For example, rejection percentage of the MR images of the chest, spine and the lower extremity is higher than the other regions of the body like head, abdomen, pelvis and neck. Accordingly, the MR images of some portions of the subject body are more prone to errors than the other regions. Accordingly, it is not only necessary to appropriately position the subject, follow correct imaging protocol, but also it is important to provide an automated guidance to the operator regarding the patient anatomy and orientation.

Figure 2:
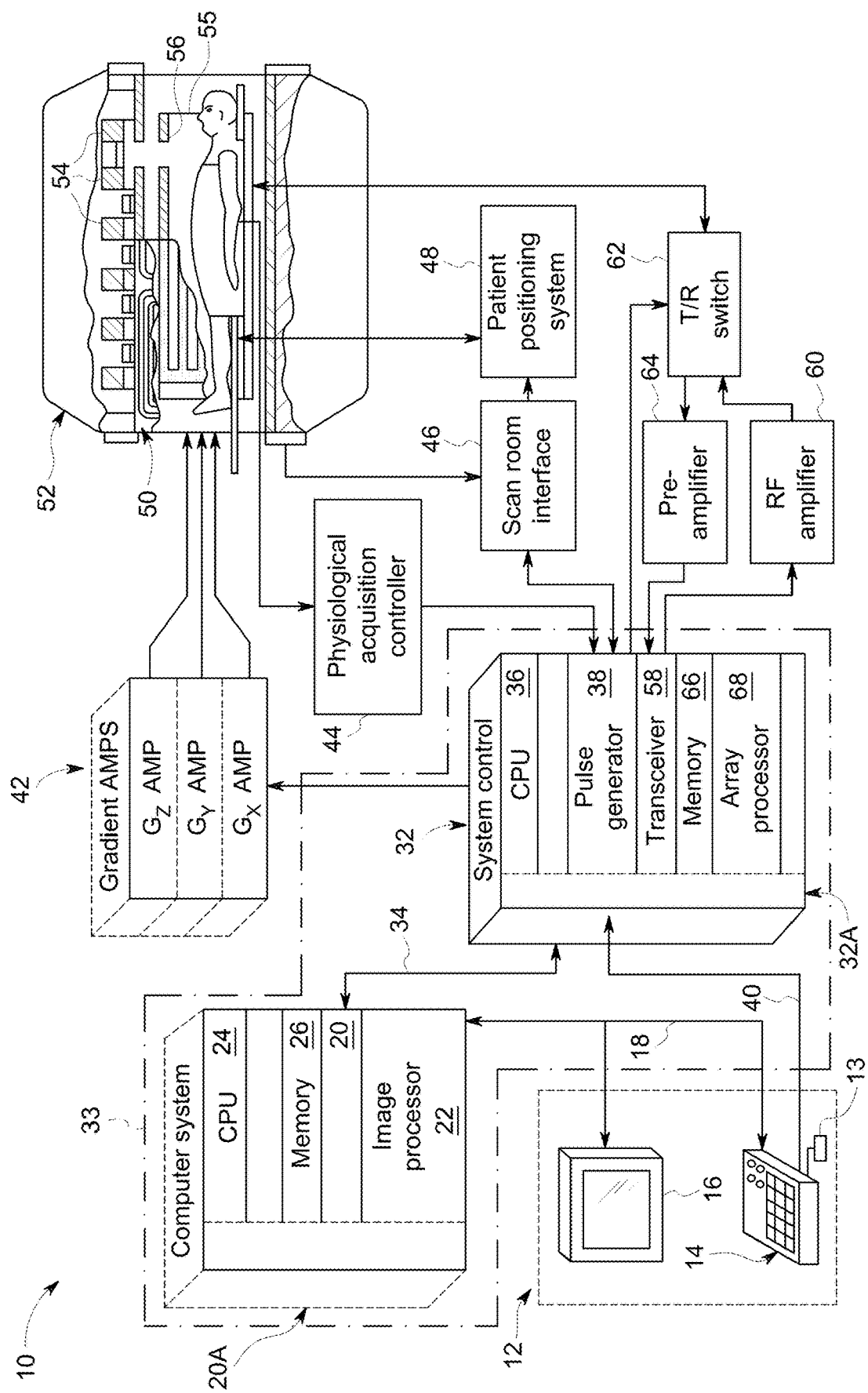
FIG. 2 illustrates an example implementation of a magnetic resonance imaging (MRI) system according to an aspect of the disclosure.

In accordance with an aspect of the disclosure, FIG. 2 shows a schematic diagram of a magnetic resonance imaging (MRI) system (10). Operation of the system (10) may be controlled from an operator console (12), which includes an input device (13), a control panel (14), and a display screen (16). The input device (13) may be a mouse, joystick, keyboard, track ball, touch activated screen, light wand, voice control, and/or other input device. The input device (13) may be used for interactive geometry prescription. The console (12) communicates through a link (18) with a computer system (20) that enables an operator to control the production and display of images on the display screen (16). The link (18) may be a wireless or wired connection. The computer system (20) may include modules that communicate with each other through a backplane (20a). The modules of the computer system (20) may include an image processor module (22), a central processing unit (CPU) module (24), and a memory module (26) that may include a frame buffer for storing image data arrays, for example. The computer system (20) may be linked to archival media devices, permanent or back-up memory storage or a network for storage of image data and programs and communicates with MRI system control (32) through a high-speed signal link (34). The MRI system control (32) may be separate from or integral with the computer system (20). The computer system (20) and the MRI system control (32) collectively form an "MRI controller" (33) or "controller". An artificial intelligence (AI) based deep learning module may be preloaded on the memory of the computer system (20). The AI based deep learning module may be trained using several MRI images to identify different anatomies. The AI based deep learning module may be trained further to identify several different objects and generate reports, images, comparative analysis of the objects for the operator of the MRI system. Further details of the structures and functioning of the AI based deep learning module has been provided along with the drawings at appropriate places in the specification.

In the exemplary embodiment, the MRI system control (32) includes modules that may be connected by a backplane (32a). These modules include a CPU module (36) as well as a pulse generator module (38). The CPU module (36) connects to the operator console (12) through a data link (40). The MRI system control (32) receives commands from the operator through the data link (40) to indicate the scan sequence that is to be performed. The CPU module (36) operates the system components to carry out the desired scan sequence and produces data which indicates the timing, strength and shape of the RF pulses produced, and the timing and length of the data acquisition window. The CPU module (36) connects to components that are operated by the MRI controller (32), including the pulse generator module (38) which controls a gradient amplifier (42), a physiological acquisition controller (PAC) (44), and a scan room interface circuit (46).

In one example, the CPU module (36) receives patient data from the physiological acquisition controller (44), which receives signals from sensors connected to the subject, such as ECG signals received from electrodes attached to the patient. The CPU module (36) receives, via the scan room interface circuit (46), signals from the sensors associated with the condition of the patient and the magnet system. The scan room interface circuit (46) also enables the MRI controller (33) to command a patient positioning system (48) to move the patient to a desired position for scanning.

A whole-body RF coil (56) is used for transmitting the waveform towards subject anatomy. The whole body-RF coil (56) may be a body coil (as shown in FIG. 1). An RF coil may also be a local coil that may be placed in more proximity to the subject anatomy than a body coil. The RF coil (56) may be a surface coil. Surface coil containing receiving channels may be used for receiving the signals from the subject anatomy. Typical surface coil would have eight receiving channels; however, different number of channels are possible. Using the combination of both a body coil (56) and a surface coil is known to provide better image quality.

The pulse generator module (38) may operate the gradient amplifiers (42) to achieve desired timing and shape of the gradient pulses that are produced during the scan. The gradient waveforms produced by the pulse generator module (38) may be applied to the gradient amplifier system (42) having Gx, Gy, and Gz amplifiers. Each gradient amplifier excites a corresponding physical gradient coil in a gradient coil assembly (50), to produce the magnetic field gradients used for spatially encoding acquired signals. The gradient coil assembly (50) may form part of a magnet assembly (52), which also includes a polarizing magnet (54) (which, in operation, provides a longitudinal magnetic field B0 throughout a target volume (55) that is enclosed by the magnet assembly 52) and a whole-body RF coil (56) (which, in operation, provides a transverse magnetic field B1 that is generally perpendicular to B0 throughout the target volume 55). A transceiver module (58) in the MRI system control (32) produces pulses that may be amplified by an RF amplifier (60) and coupled to the RF coil (56) by a transmit/receive switch (62). The resulting signals emitted by the excited nuclei in the subject anatomy may be sensed by receiving coils (not shown) and provided to a preamplifier (64) through the transmit/receive switch (62). The amplified MR signals are demodulated, filtered, and digitized in the receiver section of the transceiver (58). The transmit/receive switch (62) is controlled by a signal from the pulse generator module (38) to electrically connect the RF amplifier (60) to the coil (56) during the transmit mode and to connect the preamplifier (64) to the receiving coil during the receive mode.

The MR signals produced from excitation of the target are digitized by the transceiver module (58). The MR system control (32) then processes the digitized signals by Fourier transform to produce k-space data, which is transferred to a memory module (66), or other computer readable media, via the MRI system control (32). "Computer readable media" may include, for example, structures configured so that electrical, optical, or magnetic states may be fixed in a manner perceptible and reproducible by a conventional computer (e.g., text or images printed to paper or displayed on a screen, optical discs, or other optical storage media, "flash" memory, EEPROM, SDRAM, or other electrical storage media; floppy or other magnetic discs, magnetic tape, or other magnetic storage media).

A scan is complete when an array of raw k-space data has been acquired in the computer readable media (66). This raw k-space data is rearranged into separate k-space data arrays for each image to be reconstructed, and each of these k-space data arrays is input to an array processor (68), which operates to reconstruct the data into an array of image data, using a reconstruction algorithm such as a Fourier transform. This image data is conveyed through the data link (34) to the computer system (20) and stored in memory. In response to the commands received from the operator console (12), this image data may be archived in a long-term storage or may be further processed by the image processor (22) and conveyed to the operator console (12) and presented on the display (16).

Figure 3:
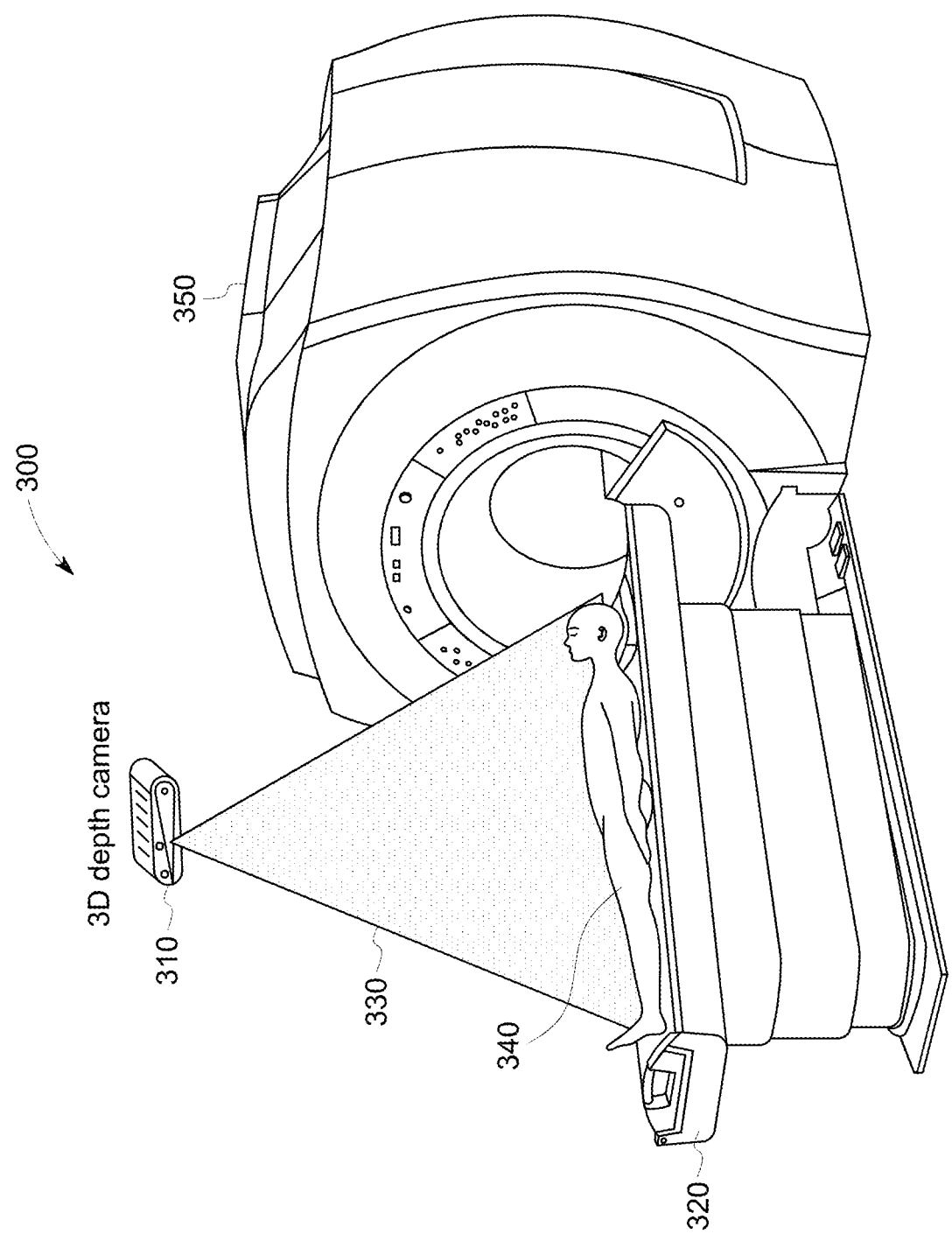
FIG. 3 illustrates an exemplary three-dimensional (3D) depth camera mounted over the table of the MRI system according to an aspect of the disclosure.

In accordance with an aspect of the disclosure, FIG. 3 shows a three-dimensional (3D) depth camera (310) mounted over the table (320) of the MRI system. The 3D depth camera (310) may be configured to detect the depth of the field of view (330) to accurately determine the table (320) boundaries and location of the subject (340) on the table (320). In one aspect, the 3D depth camera (310) may contain an infrared light emitting source and a detector of an infrared light for sending and detecting the infrared light from the camera (310). The 3D depth camera may be mounted at multiple different locations with respect to the MRI system (350) within the scanning room. Some non-limiting examples of the location of the 3D depth camera (310) include ceiling of the room, side walls, stand mount, scanner mount or lateral mount. While mounting the 3D camera (310), the 3D camera (310) may be tested for color model (Red-Green-Blue or RGB), depth and infrared streaming. Appropriate firmware for processing the image data may be installed on the 3D camera (310) that may be periodically updated.

Figure 4:
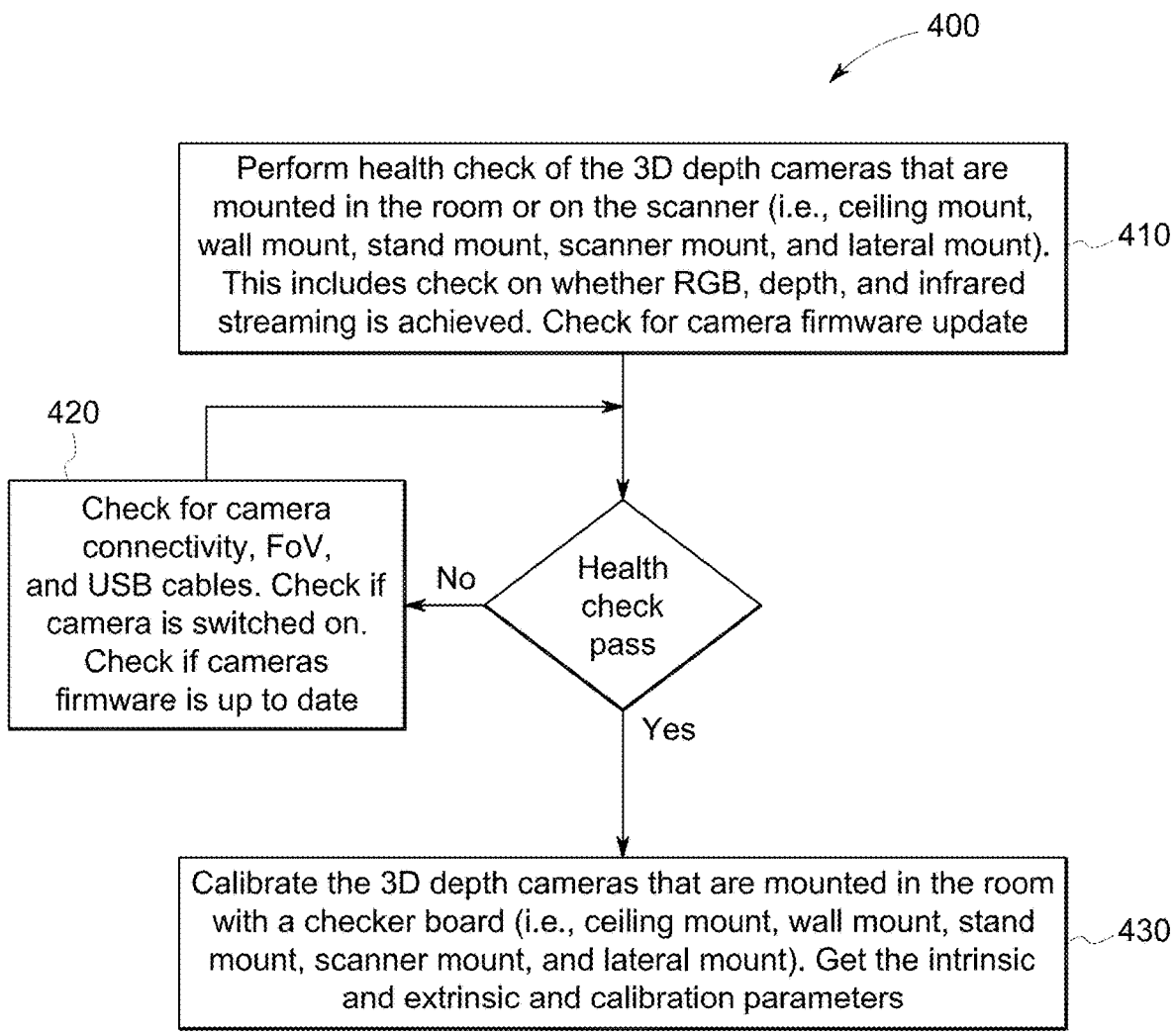
FIG. 4 illustrates a method for conducting the health-check of the 3D camera according to an aspect of the disclosure.

In accordance with an aspect of the disclosure, FIG. 4 shows a method (400) for conducting the health-check of the 3D camera (310). The method (400) includes checking (410) whether the camera settings like color model (RGB), depth, infrared and firmware update are achieved. If it is observed that any of the settings are not achieved, the method (400) includes checking (420) the 3D camera for connectivity, field of view, USB cables and firmware update. Once the camera settings are achieved, the method (400) includes calibrating (430) the different cameras within the room for imaging and obtaining the coordinates of the table, subject, and table midpoint.

Figure 5:
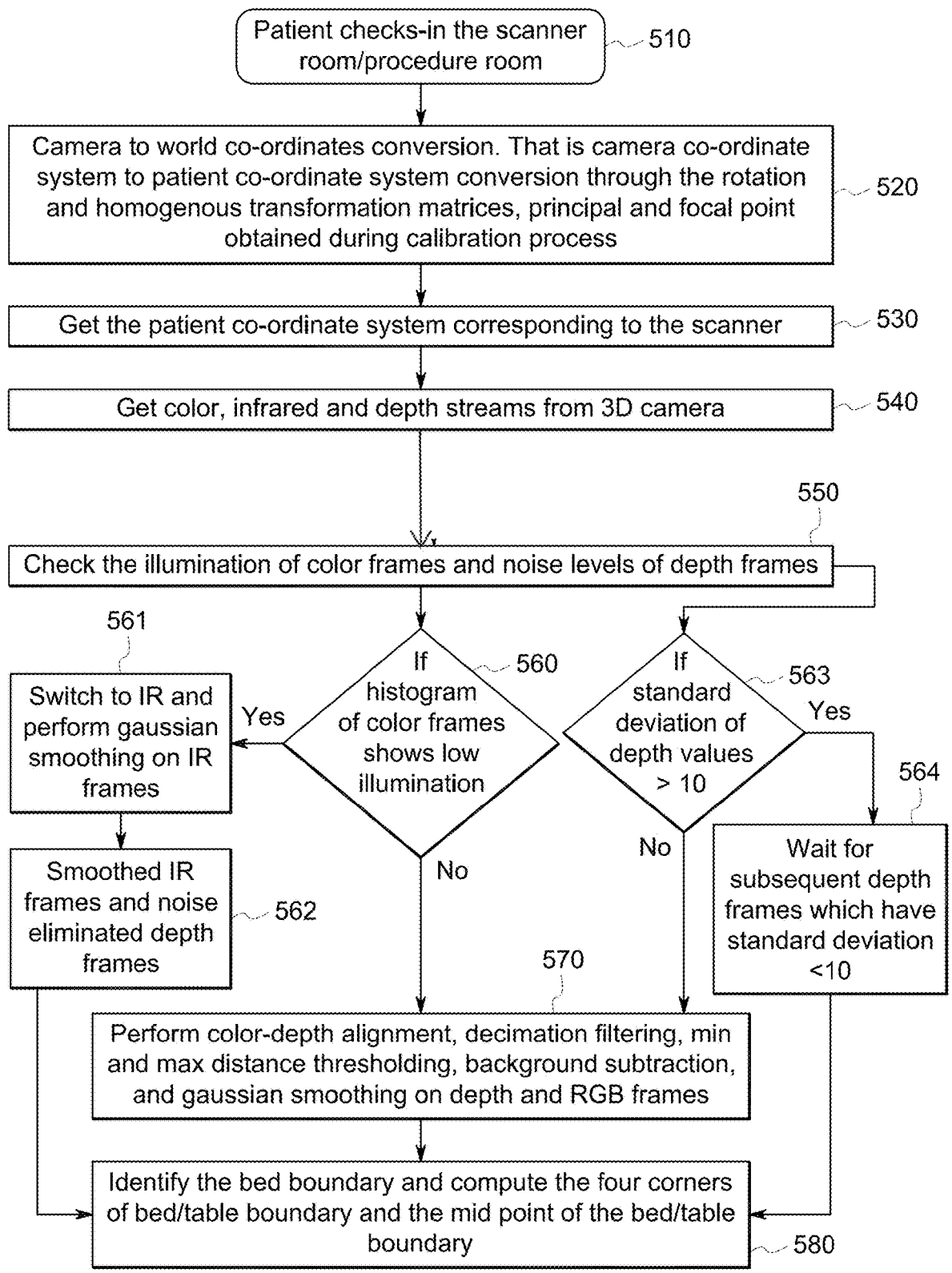
FIG. 5 illustrates a method to identify the table boundary, computing the four corners of the table and mid-point of the table of the MR imaging system according to an aspect of the disclosure.

In accordance with an aspect of the disclosure, FIG. 5 shows a method (500) to identify the table boundary, computing the four corners and mid-point of the table. The method (500) includes the subject checking-in (510) the imaging room for scanning along with the imaging prescription. The method (500) includes converting (520) the camera coordinates to the world coordinates for accurately locating the subject on the imaging table of the MRI system. Converting (520) the coordinates to the world coordinates includes converting from the camera coordinate system to the subject coordinate system using the rotation and the homogeneous transformation matrices, principle and focal points obtained during the calibration (430) of the 3D camera. The method (500) further includes generating (530) the patient coordinates with the respect to the MR imaging system. Generating (530) the patient coordinates with respect to the MR imaging system includes identifying the location and orientation of the subject with respect to the MR imaging system. The method (500) includes activating (540) the 3D camera to get the color, infrared and depth imaging streams from the 3D camera. The method (500) further includes checking (550) illumination of color frames and noise levels from the depth frames obtained by the 3D imaging camera. The method (500) includes checking (560) the histogram values of the color frames for illumination. If the illumination levels in the scanning room are enough for imaging, further image processing (570) including color-depth alignment, decimation filtering, minimum and maximum distance thresholding, background subtraction, gaussian smoothening on depth and RGB frames may be carried out.

The method (500) further includes identifying (580) the table boundary, computing the corners and mid-point of the table based on the image processing (570). During checking (560), if it is observed that the illumination levels are not enough, the method (500) includes switching (561) the camera to an infrared mode and performing gaussian smoothening on the infrared image frames obtained by the 3D camera. The method (500) further includes smoothening (562) the infrared frames to generate the smoothened infrared frames and noise eliminated depth frames. These smoothened infrared frames and the noise eliminated depth frames may be processed for identifying (580) the table boundary, computing the corners and mid-point of the table. Another image quality parameter for the images obtained by the 3D camera includes defining (563) the standard deviation of the depth values. If the standard deviation of the depth frames is less than ten (<10), further image processing (570) including color-depth alignment, decimation filtering, minimum and maximum distance thresholding, background subtraction, gaussian smoothening on the depth and RGB frames may be carried out. However, if the standard deviation of the depth frames has a value greater than ten (>10), the method (500) includes waiting (564) for the subsequent depth frames from the 3D camera that have a standard deviation value of less than ten (<10) before further image processing (570) for identifying the table boundary and mid-point of the table. Using the identified boundary and mid-point of the table of method (500), an artificial intelligence (AI) module may be trained to identify the table boundary and mid-point of the table.

Figure 6:
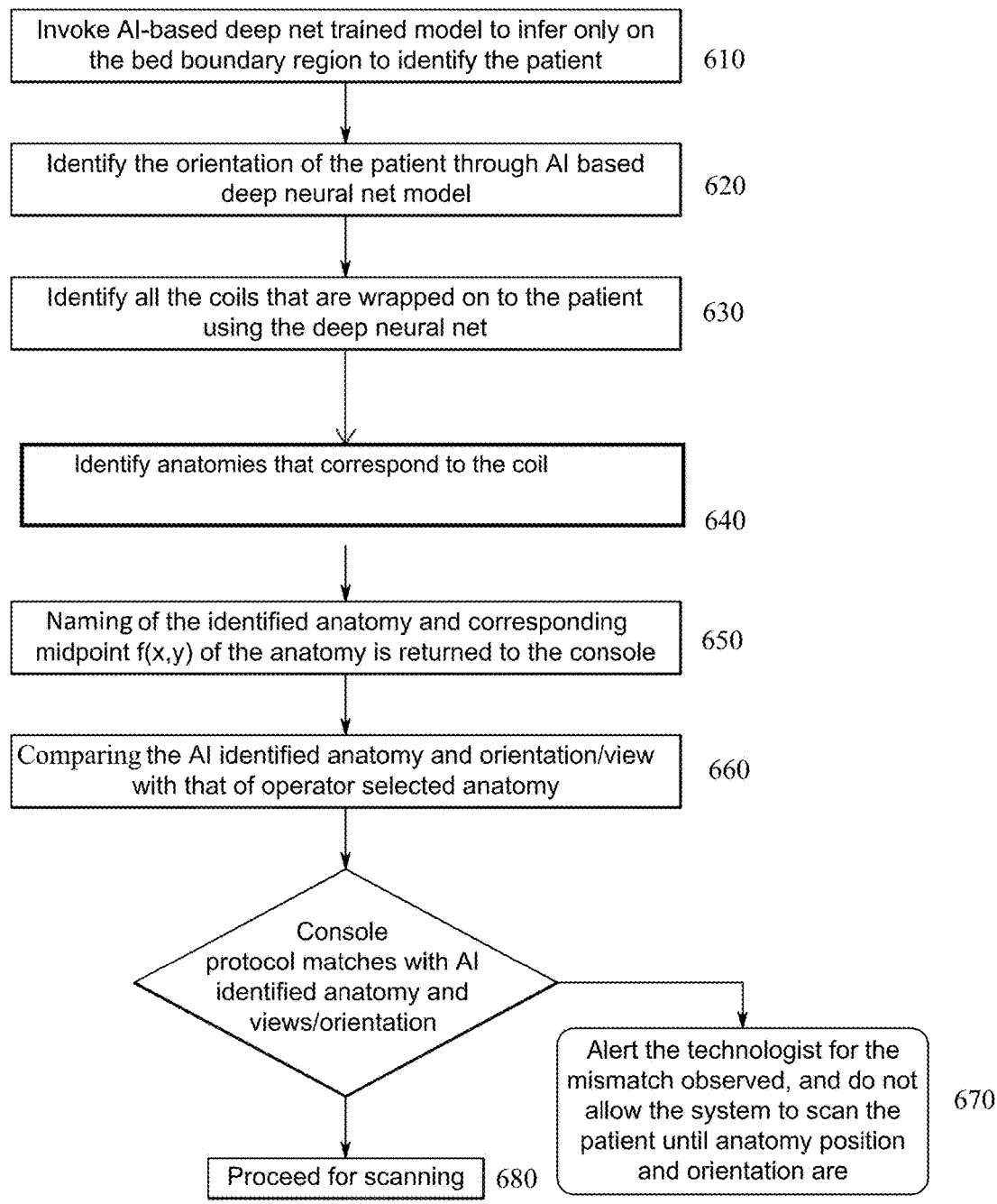
FIG. 6 illustrates a method for MR table identification, orientation of the subject, identification of the RF coils and identification of the anatomy using the artificial intelligence (AI) based deep learning module according to an aspect of the disclosure.

In accordance with an aspect of the disclosure, FIG. 6 shows a method (600) for MR table identification, orientation of the subject, identification of the RF coils and identification of the anatomy using the artificial intelligence (AI) based deep learning module. In one aspect, the method (600) includes employing (610) an AI based deep learning (DL) module to identify the boundaries of the table. The method (600) further includes (620) identifying the orientation of the subject through AI based deep neural net model. Examples of the orientation of the subject include head-first, feet first, supine prone, left decubitus and right decubitus. The method (600) further includes identifying (630) the imaging coils wrapped around the subject body using the DL module. Multiple imaging coils may be simultaneously wrapped around the subject body for imaging and the method (600) includes identifying (630) the different coils wrapped around the subject body using the AI based deep learning module. Some non-limiting examples of the imaging coils include head coil, chest coil, leg coil or a full body coil. When different coils are identified (630) by the AI based deep learning module, the method (600) further includes identifying (640) all the anatomies corresponding to the coil. In one example, if the AI based deep learning module identifies a particular RF-coil as the head coil, the AI based deep learning module will provide details of the orientation of the head. The method (600) further comprises naming (650) the identified anatomy and displaying the coordinates f(x, y) of the mid-point of the anatomy on the operator console. The operator of the MR imaging system may manually select and position the imaging coils over the subject anatomy and the method (600) further includes comparing (660) the DL module identified anatomy and orientation of the subject with the operator selected anatomy and corresponding coils. The operator selected imaging protocol may be inputted to the computer system through the console for comparison with the imaging protocol preloaded on the AI based deep learning module. If the imaging protocol selected by the operator doesn't match with the AI based deep learning module identified protocol, the method (600) includes alerting (670) the operator for mismatch of the operator protocol with the AI based deep learning module identified protocol and not allowing the MR imaging system to scan until the anatomy position, orientation of the subject and position of the imaging coils match the AI based deep learning module identified protocol. The method (600) further includes scanning (680) the subject when the AI based deep learning module identified protocol matches the protocol selected by the operator.

Figure 7:
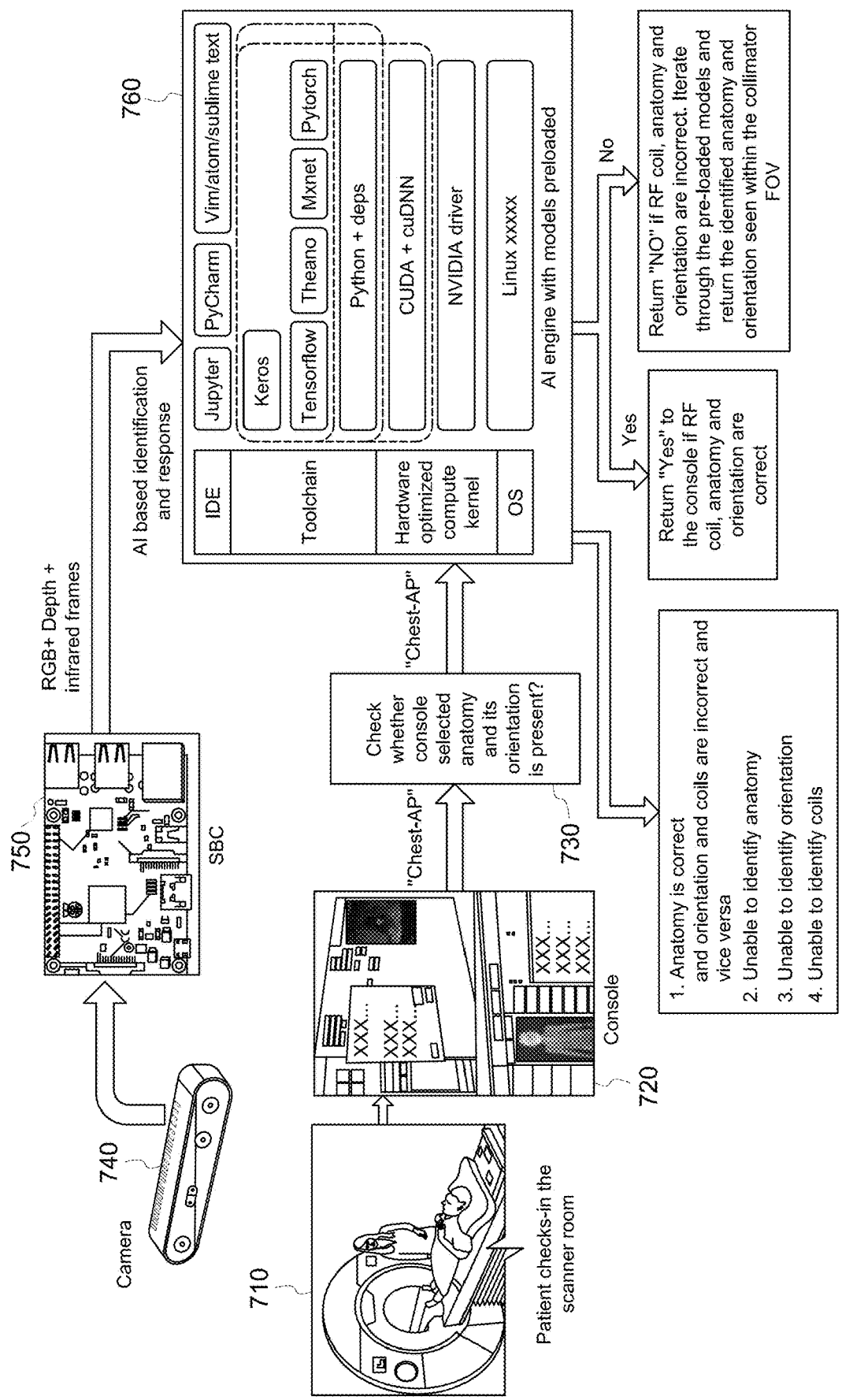
FIG. 7 illustrates a method for automated subject anatomy and orientation identification by a three-dimensional (3D) depth camera using the artificial intelligence (AI) based deep learning module according to an aspect of the disclosure.

In accordance with an aspect of the disclosure, FIG. 7 shows a method (700) for automated subject anatomy and orientation identification by a three-dimensional (3D) depth camera using the artificial intelligence (AI) based deep learning module. FIG. 7 is a visual representation of the method (600) of FIG. 6. The method (700) includes the subject checking-in (710) the scanning room for imaging along with the imaging prescription. The method (700) includes selecting (720) the imaging protocol by the operator over the console and checking (730) manually by the operator whether the console selected anatomy and its orientation is present on the table. The operator selected protocol is inputted to the AI based deep learning module. The method (700) further includes capturing (740) using the 3D camera, the subject orientation and position of the RF coils over the anatomy. The method (700) further includes processing (750) the images captured by the 3D camera for color model (RGB), depth and infrared frame checks and inputting these images to the AI based deep learning module. The method (700) further includes comparing (760) by the AI based deep learning module the imaging protocol inputted by the operator to the orientation images and coil images received from the 3D camera to determine if the operator has accurately placed the correct type of coils over the prescribed anatomy as per the imaging protocol. The AI engine is preloaded with the imaging protocols to decide the orientation of the subject and accuracy of the placement of the coils over the anatomy. In one example, when the operator has correctly identified the anatomy, but wrongly identified the orientation and placed the coils, the AI module will provide an output showing the correct identification of the anatomy but wrong orientation and placement of the coils. In another example, if the anatomy and the orientation of the subject is correctly identified by the operator along with the accurate placement of the imaging coils, the AI module will provide an output indicating accurate identification of the anatomy, orientation and placement of the coils.

Figure 8:
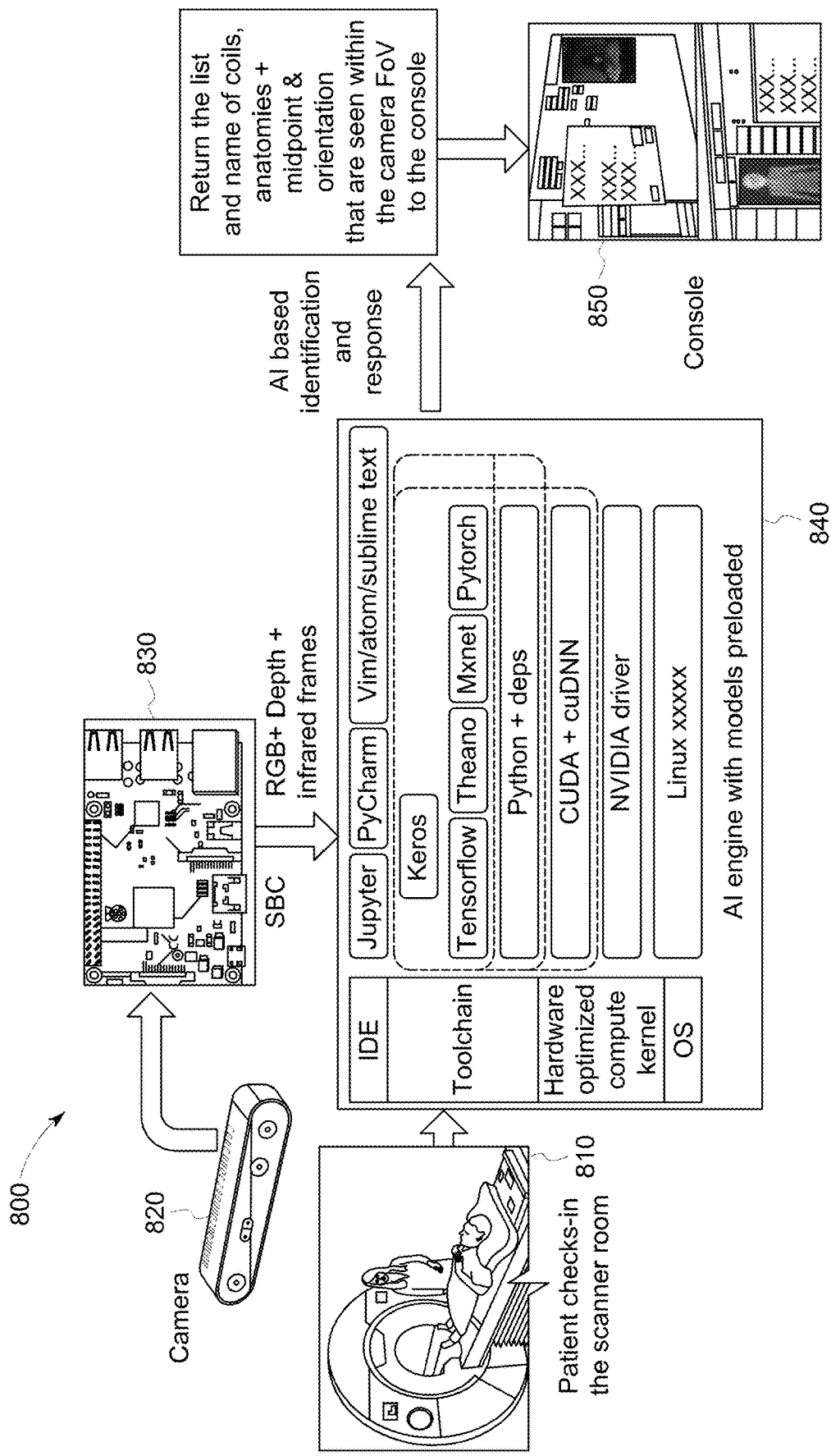
FIG. 8 illustrates a method for automated patient anatomy and orientation identification by a three-dimensional (3D) depth camera using the artificial intelligence (AI) based deep learning module according to another aspect of the disclosure.

In accordance with an aspect of the disclosure, FIG. 8 shows a method (800) for automated patient anatomy and orientation identification by a three-dimensional (3D) depth camera using an AI based deep learning module. The method (800) includes the subject checking-in (810) in the MRI scanning room and lying down on the table. The method (800) further includes capturing (820) images of the subject using the 3D camera to obtain the details of the patient anatomy, orientation and coils used for imaging the subject. The method (800) further includes processing (830) the images captured by the 3D camera for color model (RGB), depth and infrared frames to identify the table boundary, patient anatomy, orientation and the RF coils and inputting these details to an AI module. The method (800) further includes processing (840) the images obtained from the 3D camera and the patient table by the AI module for AI based identification of the anatomy, orientation and coils to generate a response. The method (800) may further include displaying (850) over the console the details of the anatomy, orientation, coils and such other details as may be necessary, for example, mid-point of the anatomy. The AI module determines if identification of the anatomy, orientation, and coils is matching the imaging protocol and displays over the console any discrepancy between the imaging protocol and the actual anatomy, orientation of the subject and placement of the coils.

The method for MRI table identification will be explained in detail. In accordance with an aspect of the disclosure, FIG. 9(*a*) shows a method of MRI table identification using the original point cloud counters extracted from the depth frames. The method (900) includes extracting (910) the table plane from other planes within depth data. This includes extracting the point cloud data corresponding to the camera's coordinate system from the depth frames of the 3D camera. FIG. 9(*b*) shows a method (920) for MRI table identification using the top-down view of the original point cloud counters extracted from the 3D depth camera. As may be seen from FIG. 9(*b*), the closest data points to the camera (for example, the patient table) and the farthest data points from the camera (for example, the ground surface) may be identified as different structures and displayed in different colors.

In accordance with an aspect of the disclosure, FIG. 9(*c*) shows a method (900) that may include MRI table identification using the point cloud data from the floor plane extracted from the depth camera. The method (900) includes extracting (930) the point cloud data in the first plane, the floor, from the rest of the point cloud data. Initially, the maximum point to plane distance may be set to the distance between camera mounted on the celling and the floor. In other words, the farthest a point can be to a plane and still be considered part of that plane may be the distance between camera and bed. The normal vector of the wanted plane may be [0,0,1] because the plane may be approximately on the x-y plane. The maximum angular distance of the plane may be set to 30°. Using the function pcfitplane( ), the point cloud data, the maximum point to plane distance, the reference vector, and the maximum angular distance the floor plane may be created. The floor plane datapoints may be set as plane1. The pcfitplane( ) may refer to [x, y, z] coordinates corresponding to the MRI bed points from which the best fitting plane may be defined. Expected format is an array which is represented by array([[x1,y1,z1], . . . [xn, yn, zn]]). In 3D Euclidean space, each plane can be expressed as (1). Therefore, according to the distribution of points and the plane function, the best-fitted plane is capable of being calculated by least square fitting (LSF). LSF uses the concept of minimizing the square sum of normal distances as (2) and (3) from all 3d points to the optimal plane to determine the parameters of the best-fitted plane. ax+by+cz+d=0 where a and b are normal of a plane (1)

$$P_i = F_i(a, b, c, d) = \frac{|ax_i + by_i + cz_i + axd_i|}{\sqrt{a^2 + b^2 + c^2}} \quad (2)$$

where $P_i$ represents the normal distance from ith point of the plane, $$\Sigma_{i=1}^m P_i^m \quad (3)$$

The point cloud plane fit method is used to compute the X Y Z planes of the MRI bed point cloud and fit the plane to the appropriate point cloud axes using LS. The point cloud plane fitting ensures that the bed points are grouped, patient may be identified within the fitted plane, and bed points are clearly delineated to the precise plane.

Figure 9A:
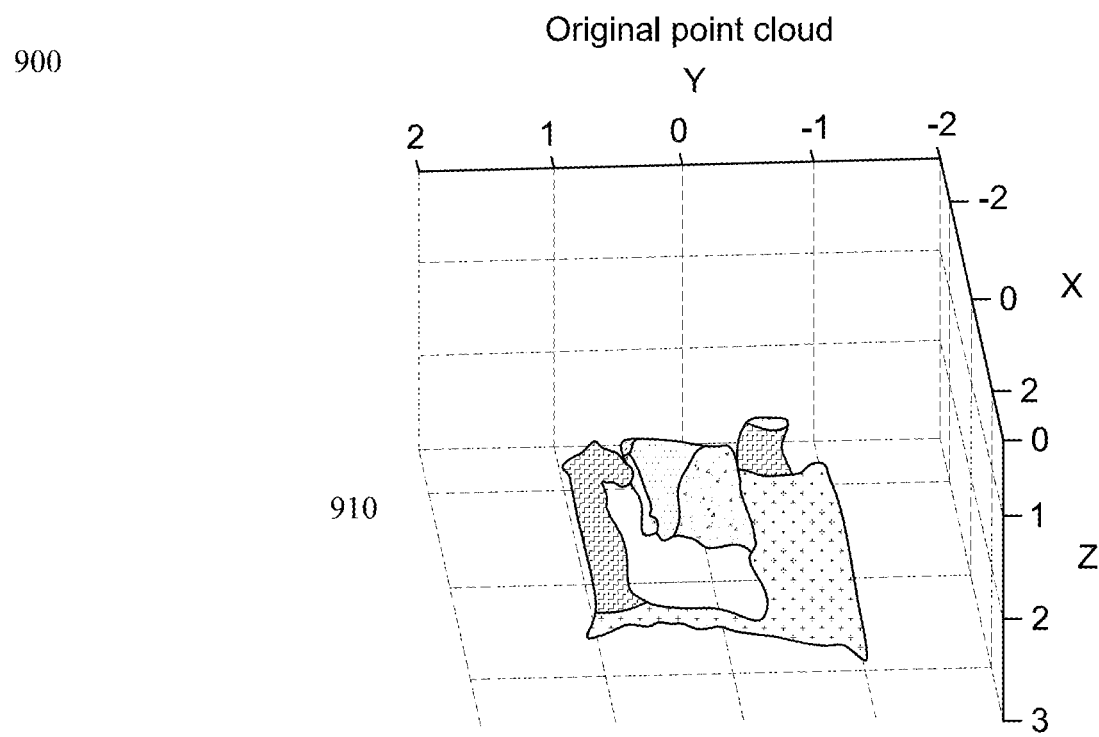
FIG. 9(a) illustrates a method for table identification of the MRI system using the original point cloud counters extracted from the depth frames according to an aspect of the disclosure.
Figure 9B:
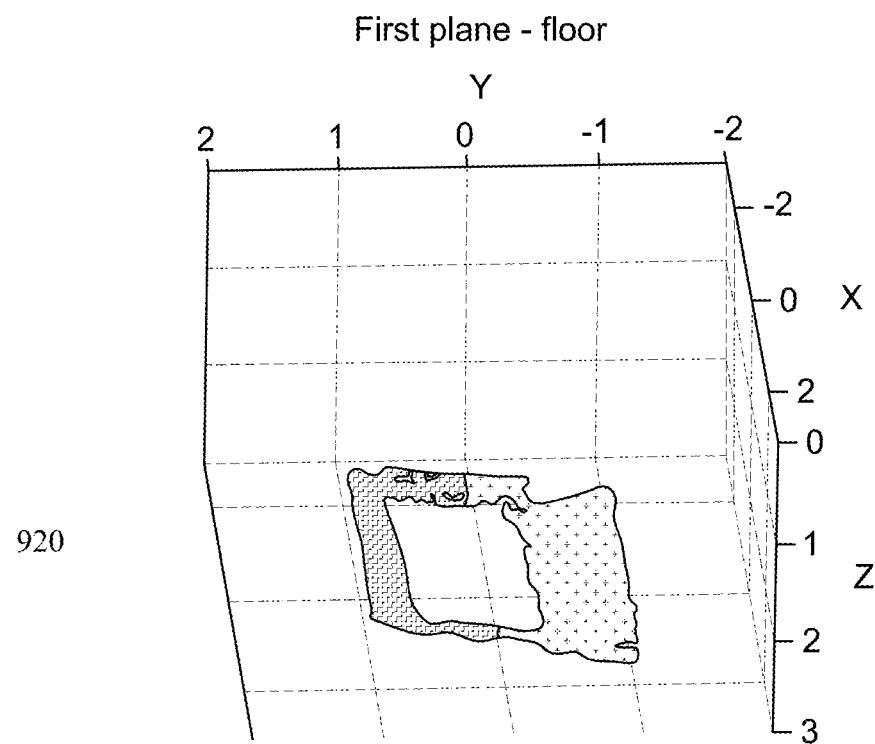
FIG. 9(b) illustrates a method for table identification of the MRI system using the top-down view of the original point cloud counters extracted from the depth camera according to an aspect of the disclosure.
Figure 9C:
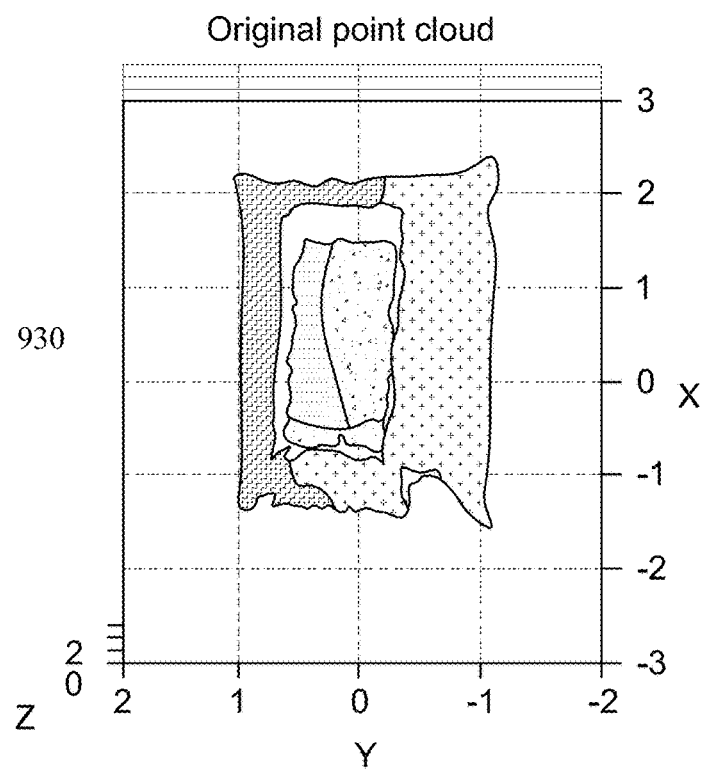
FIG. 9(c) illustrates a method for table identification of the MRI system using the point cloud data from the floor plane extracted from the depth camera according to an aspect of the disclosure.
Figure 9D:
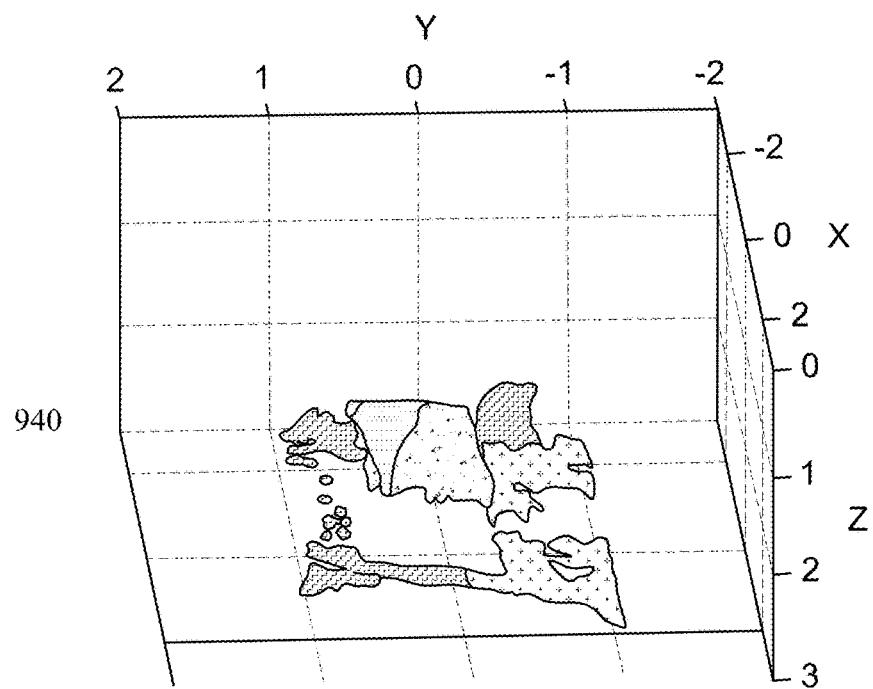
FIG. 9(d) illustrates a method for table identification of the MRI system using the point cloud data without the floor plane extracted from the depth camera according to an aspect of the disclosure.

In accordance with an aspect of the disclosure, FIG. 9(d) shows a method (900) that may include MRI table identification using the point cloud data with the floor plane extracted from the depth camera. The method (900) includes displaying (940) the remaining point cloud data after floor removal. Some points that should have been considered part of the floor plane are not shown because of noise and the maximum point to plane distance value. Further, it may not be necessary to extract the floor plane to extract the table plane from the data.

Figure 9E:
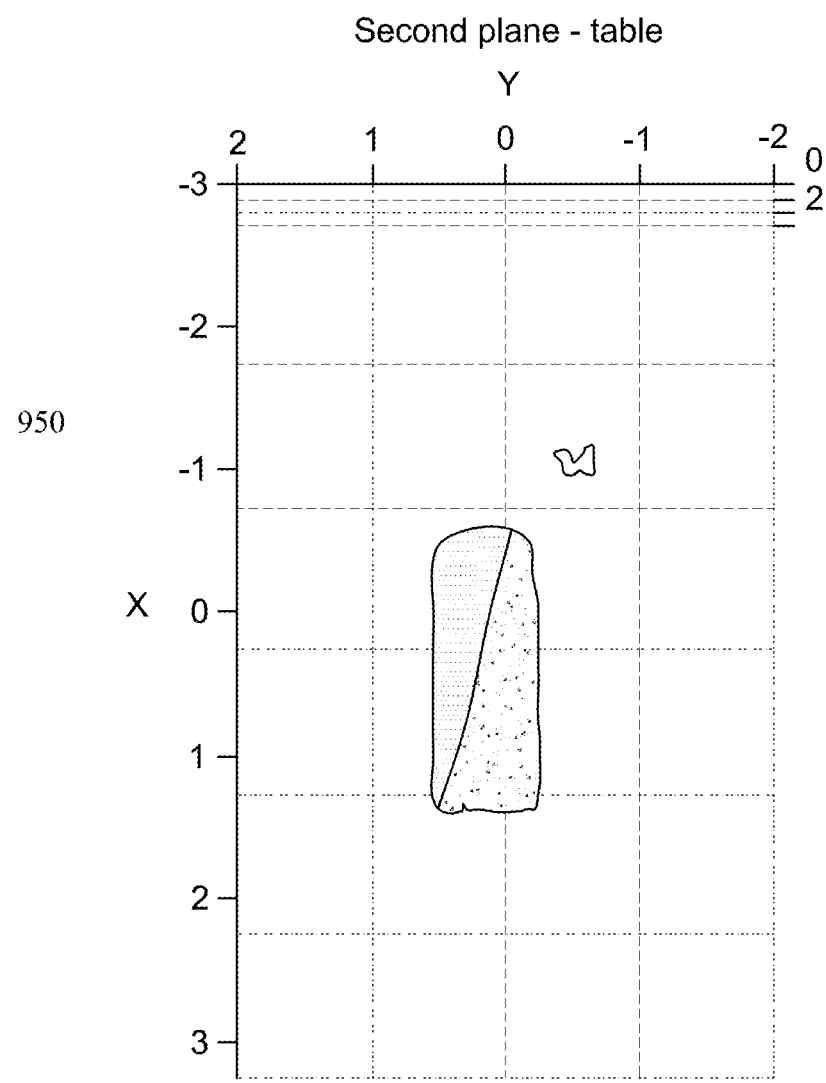
FIG. 9(e) illustrates a method for table identification of the MRI system using the point cloud data in table plane using the depth camera according to an aspect of the disclosure.

In accordance with an aspect of the disclosure, FIG. 9(e) shows a method (900) MRI table identification using the point cloud data in table plane using the depth camera. The method (900) includes extracting (950) the point cloud data in the second plane, the table, from the remaining point cloud data. To extract the table, a region of interest may be used to narrow down the "z" location of the table. The region of interest takes into consideration any point that may be located within two meters of distance or closer to the camera. The function pcfitplane( ) may be used again with the same maximum point to plane distance but in conjunction with the remaining point cloud data and the indices of points within the region of interest. The table plane data points are set as planet or the normal plane of the point cloud. The four corners of the bed boundary and its midpoint is computed using second plane. All the subsequent intelligent processing such as AI based deep neural network-based coil identification, patient identification, orientation and anatomy identification are performed within the four corners of the bed boundary. Whenever the depth is noisy and point cloud is not faithfully extracted, an AI based shape detection neural network identifies the table boundary and outputs the four corners of the table boundary. The table boundary extraction is applicable to both docking and non-docking MRI patient table.

Figure 10A:
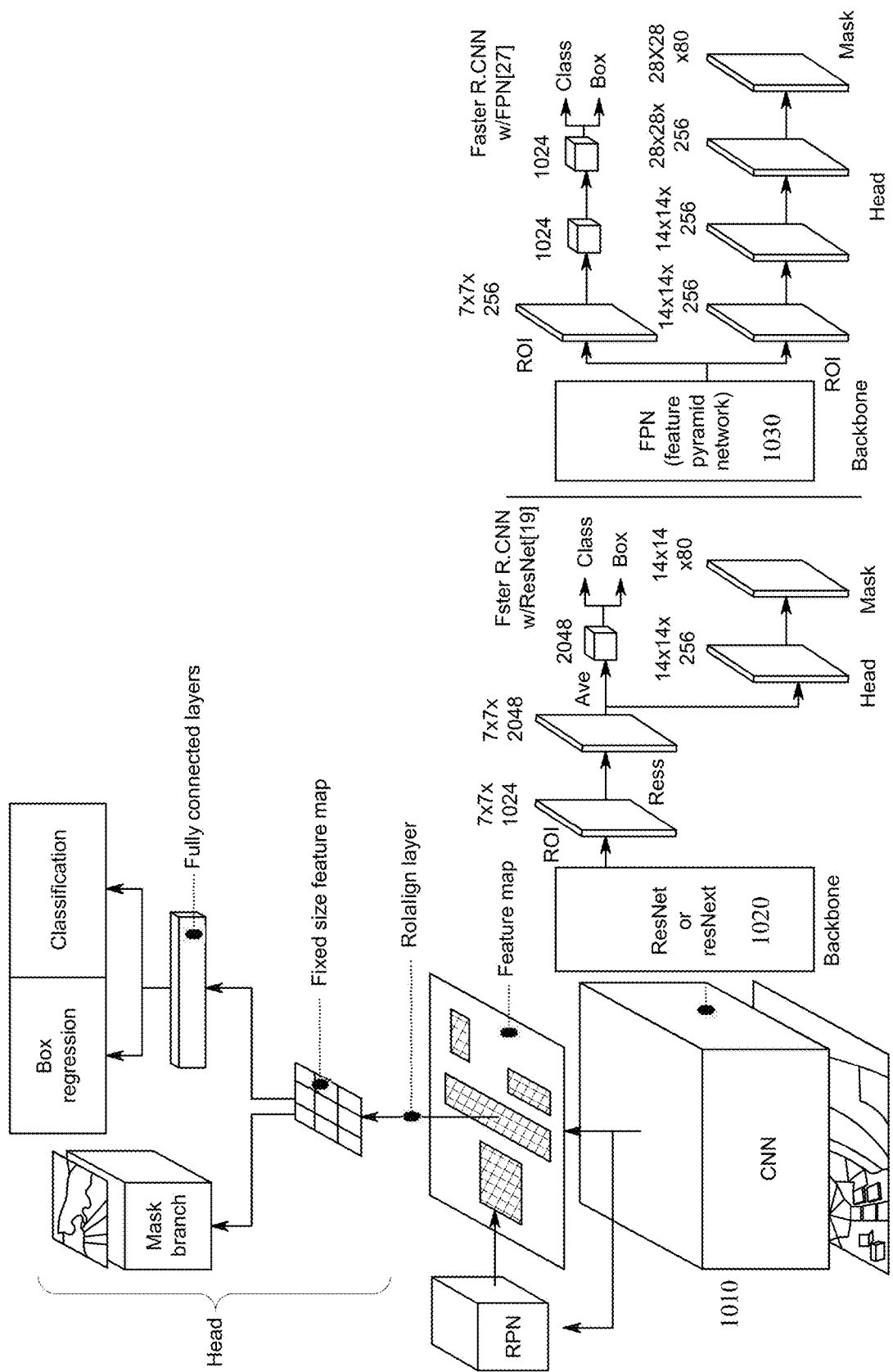
FIG. 10(a) illustrates artificial intelligence (AI) based deep learning module for identification of the patient according to an aspect of the disclosure.

In accordance with an aspect of the disclosure, FIG. 10(a) shows artificial intelligence (AI) based deep learning module for identification of the patient. Prior to placement of the imaging coils on the subject, it is necessary to identify if the subject is lying down within the boundaries of the table. The boundaries of the table and four corner points of the table may be decided according to the method (900) explained with reference to FIGS. 9(a)-9(e). The images of the subject may be obtained using the 3D camera and an AI based subject key point algorithm may be employed to decide if the patient is lying down within the four corner points of the bed boundary that was computed using the point cloud. Further, the FIG. 10(a) shows the architecture of the AI-based deep learning module for the regions-based identification of anatomical area and coils. The input image from the camera which is combination of colorized depth and RGB color frames is fed to a region proposal convolution neural network (RP-CNN) (1010) which identifies the patient, patient mask, mask of the coils and anatomical area of patient. Once the mask region is identified appropriately, features are extracted within the mask using region-based pooling and region of interest alignment method. Multiple probable regions where the object of interest could be present may be queried and bounding boxed are populated to each of the probable regions. These probable regions are then passed to convolutional neural network. The backbone of this convolutional neural network may a residual network (ResNet) (1020) which is responsible for determining the class of the probable object regions and then highlight each class area with a bounding region of interest mask. Whenever the residual network fails to identify certain complex features, another backbone known as feature pyramid network (FPN) (1030) is invoked to align the region of interest. After alignment, the region proposal network (1010) generates the masking area of the probable regions where the object of interest may be present.

Figure 10B:
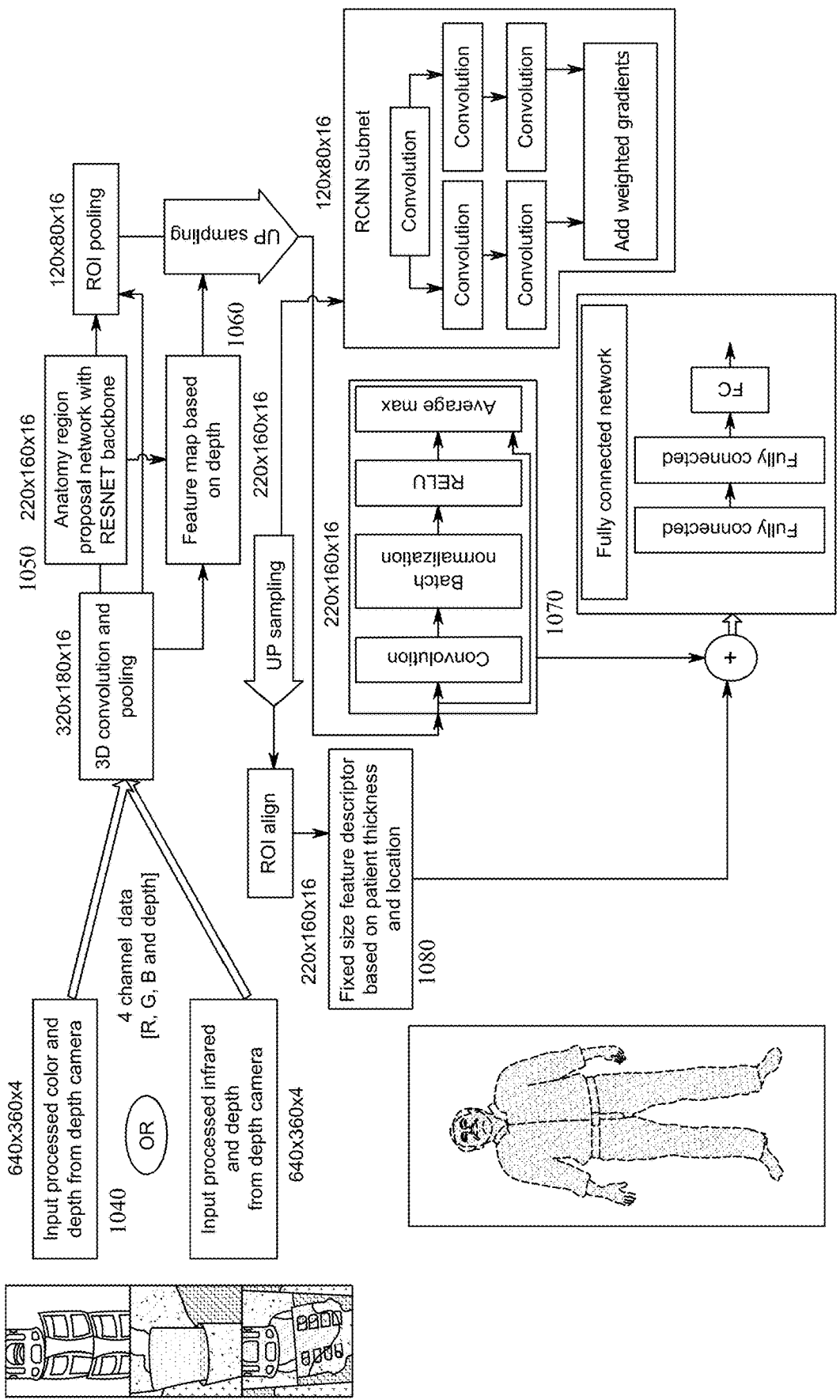
FIG. 10(b) illustrates artificial intelligence (AI) based deep learning module for identification of the patient according to an aspect of the disclosure.

In accordance with an aspect of the disclosure, FIG. 10(b) shows an artificial intelligence (AI) based deep learning module for identification of the patient. FIG. 10(b) uses the entire AI module architecture of FIG. 10(a) as the processing block. The colorized depth input and depth frames (1040) are aligned to extract patient contour in occlusion and non-occlusion states. According to an aspect of the disclosure, as show in FIG. 10(b), the AI based deep learning module is used to identify whether the patient is present within the occluded coils. To perform the patient identification, the network of FIG. 10(b) computes the probable anatomical region co-ordinates and these co-ordinates may be further fed to a region proposal network (1050) in a fixed batch size. Each batch may consist of approximately fifty region-based proposal mask/shape of the patient. The feature map (1060) may be extracted from the depth information of the probable patient masks and then fed to a plurality of cascaded multiple convolutional neural network blocks (1070) for identification. Once the region is confidently identified, the presence of patient in the region may be validated through feature descriptor-based vector (1080) which computes the average thickness of the probable patient regions and gives a final confident score of the patient's presence.

Acquisition, processing, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine learning can be used to help configure, monitor, and update the medical imaging workflow and devices.

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

In certain examples, deep learning and/or other machine learning networks can be configured to determine an image acquisition prescription or otherwise form a data structure to instantiate parameters/settings for image acquisition based on a desired image quality (IQ). In certain examples, multiple deep learning networks are used to generate an image acquisition prescription. For example, a first network (e.g., a regression network, etc.) computes image acquisition prescription parameters based on the desired IQ and scan time chosen (e.g., chosen by a user, specified by a program, imaging protocol, and/or other system, etc.) to form an image acquisition "prescription" or configuration data structure. A regression network is lighter weight and less computationally intensive compared to a deep learning network, for example.

An image preview can be generated of an image that has an IQ closest to the image acquisition prescription (e.g., computed by the first network). A second network (e.g., a deep learning network, etc.) learns IQ metrics periodically from obtained site images and updates the first network to improve the first network's generation of corresponding image acquisition parameters. The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

Figure 11:
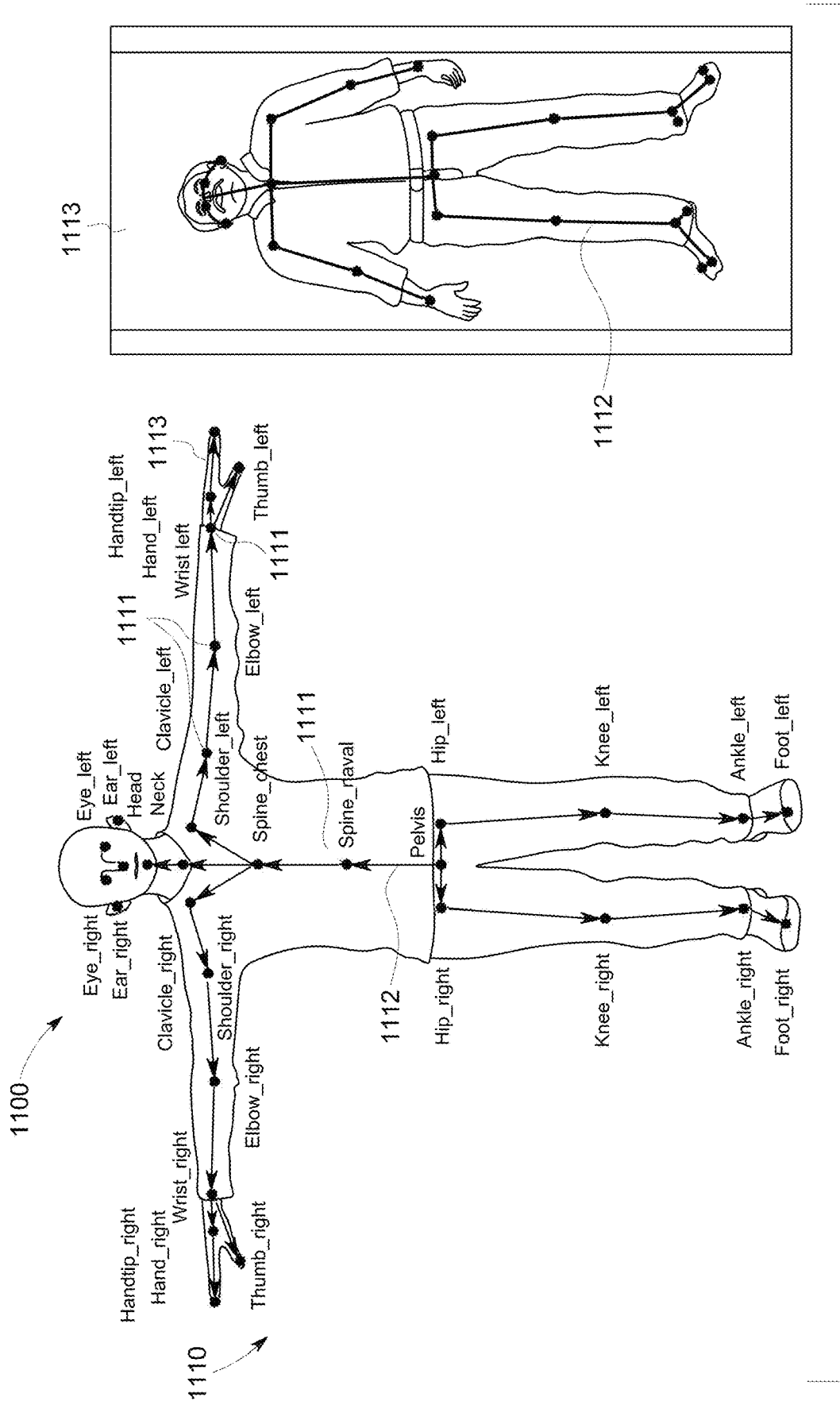
FIG. 11 illustrates a method for identification of the key anatomical points before the placement of the coil according to an aspect of the disclosure.

In accordance with an aspect of the disclosure, FIG. 11 shows a method (1100) for determining (1110) the key points (1111) that define the anatomical points of the subject before the placement of the RF coils. Once the RF coils are mounted on the subject body, the anatomy of the subject may not be visible to the operator or the camera. In such situation, the ability of the AI module to automatically determine the accurate placement of the coils over the appropriate anatomy may be hampered. This problem may be addressed by defining the key anatomical points (1111) corresponding to various organs of the patient before the placement of the RF coils. Once the key anatomical points (1111) are marked, grid lines (1112) may be used to connect these key points (1111) and generate a torso image (1113) of the subject for anatomy identification. Identifying the key anatomical points and orientation of patient regions may depend on the regions occluded by blanket, hospital gown or any kind of cover over the subject body while determining the accurate positioning of the RF coils of the MRI system over the subject anatomy for imaging. Various type of RF imaging coils may be occluded by blanket, hospital gown and covers and identifying the RF coils is important for accurate localization and automated landmarking during MRI exams.

The torso image (1113) of the subject defines anatomical shapes, their dimensions and identifies the location of the organs to determine accurate placement of the RF coils over the anatomy. Generating the torso image (1113) includes identifying the key points (1111) on the subject corresponding to various organs and anatomical regions and connecting the key points (1111) to generate the torso image (1113) of the subject. When the imaging coils such as RF coils are wrapped around the subject body for imaging, organs of the subject may not be present in the field of view (FoV) of the camera for imaging. In order to determine the accurate placement of the imaging coils over the subject body surface, the torso image (1113) may be used as the simulation of the subject body and coordinates of the RF coils may be mapped to the location of the subject organs over the torso image (1113).

Figure 12:
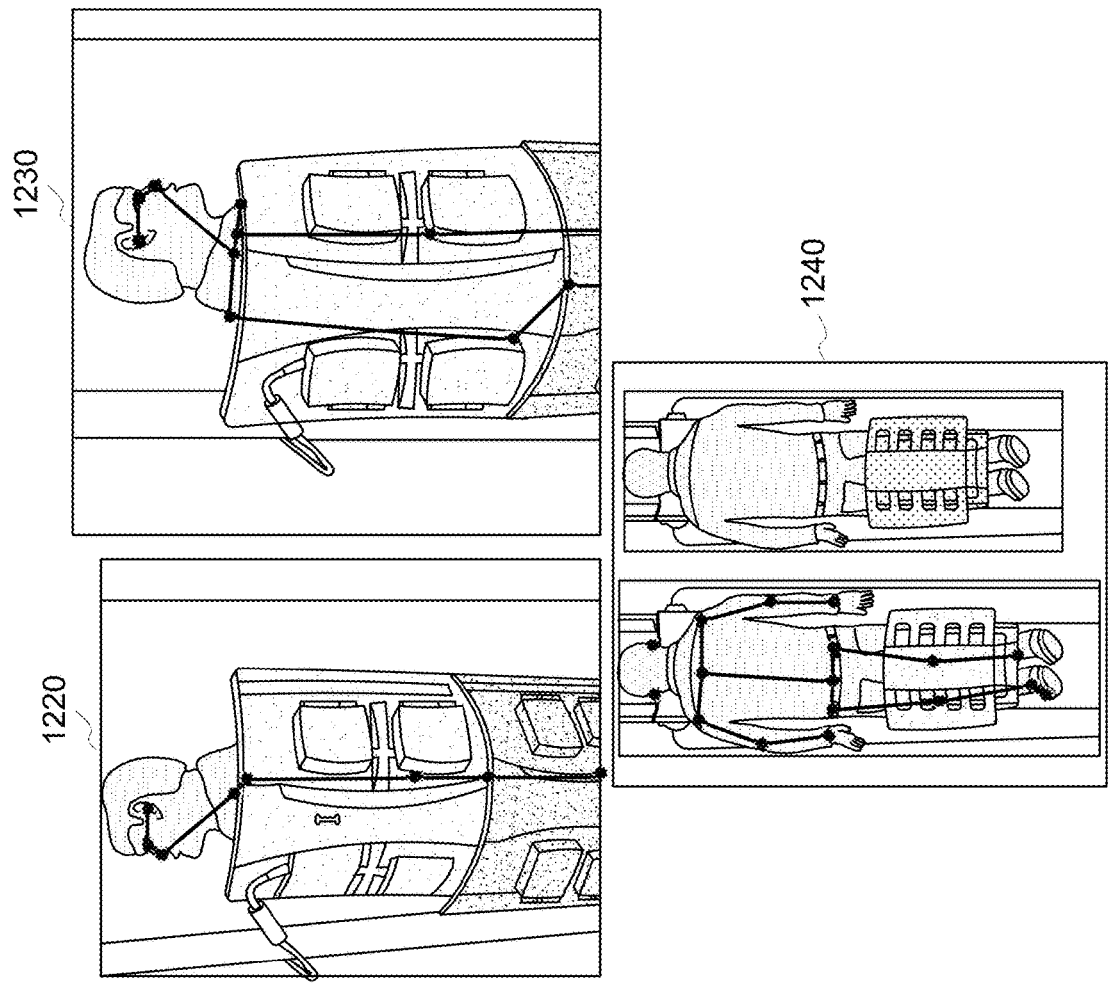
FIG. 12 illustrates an AI based orientation identification of the subject using shapes and thickness according to an aspect of the disclosure.
Figure 12:
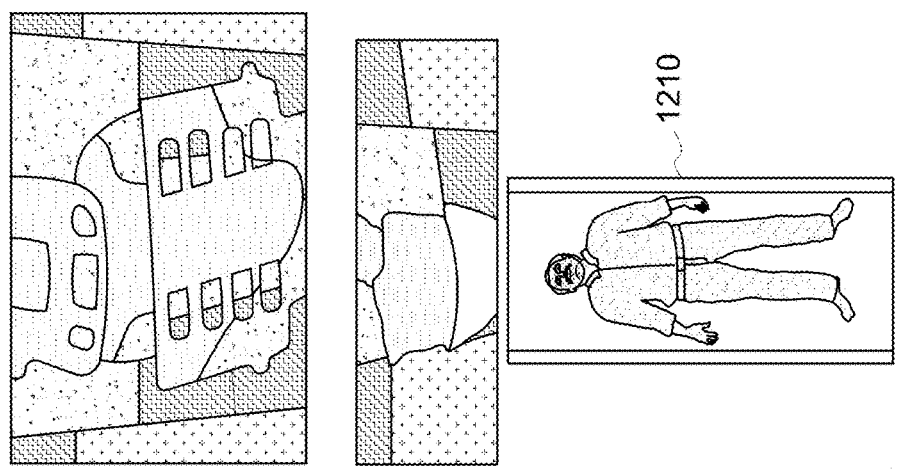

In accordance with an aspect of the disclosure, FIG. 12 shows AI based orientation identification the subject using shapes and thickness. The subject may be placed on the table in various orientations based on the imaging requirement prescribed for the subject. Various subject placements on the table include, for example head-first supine (1210), left decubitus (1220), right decubitus (1230) and head-first prone (1240). Determining the accurate placement of the imaging coils over the anatomical region of the subject may require identifying the orientation of the subject. Once the table boundary and the key point-based patient identification is performed, the patient orientation identification may be performed. The AI module may be configured to determine the orientation of the subject and generate an image of the subject over the console to identify the orientation of the subject. The AI module may be further configured to identify the mismatch between the prescribed orientation of the subject and actual orientation of the subject obtained by using the 3D imaging camera. When any mismatch between the prescribed orientation and the actual orientation of the subject is observed, the AI module may be further configured to prescribe the necessary changes in the subject orientation to the operator till the prescribed orientation of the subject is achieved.

Figure 13:
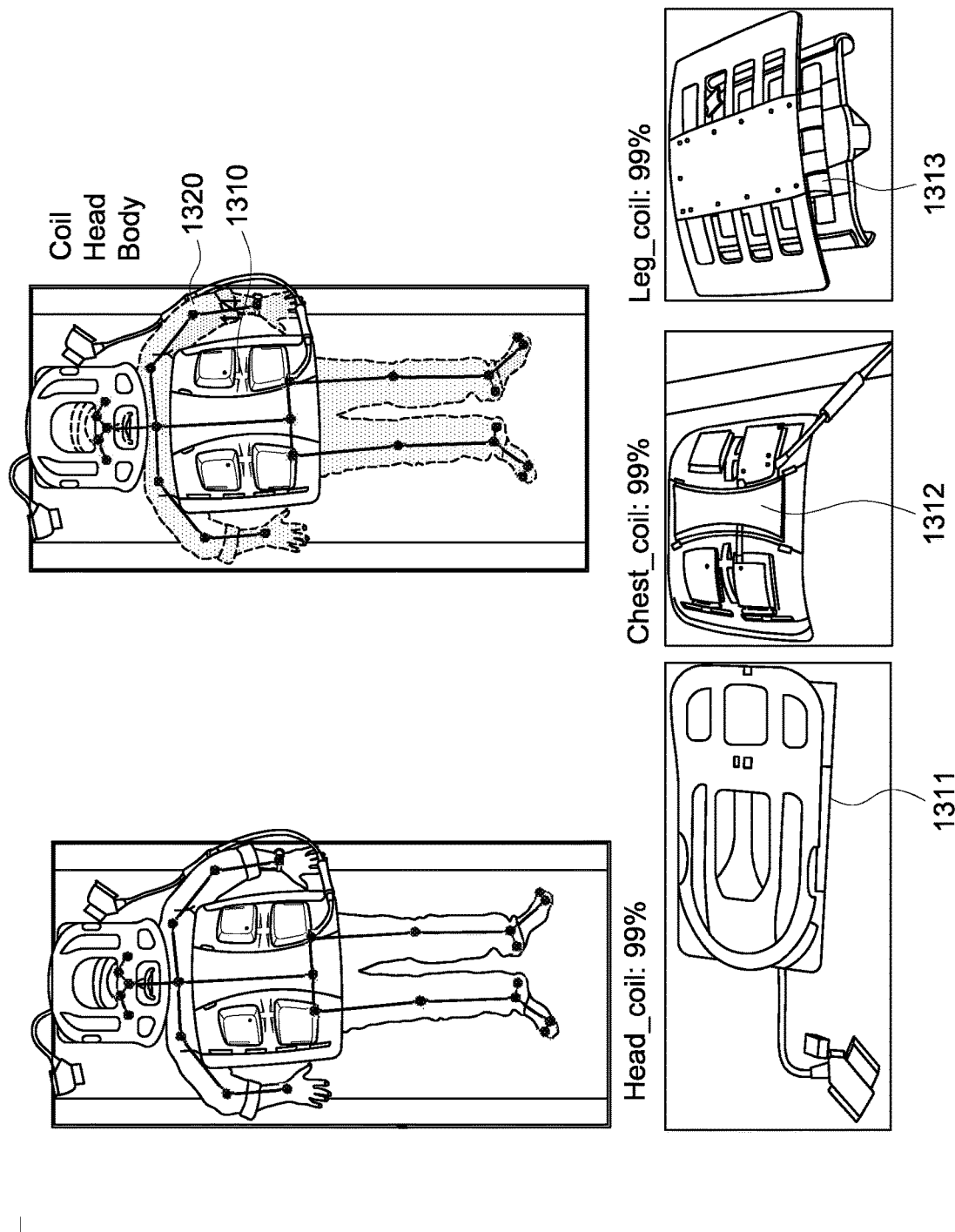
FIG. 13 illustrates an AI based identification of the RF coils of the MRI system according to an aspect of the disclosure.
Figure 14:
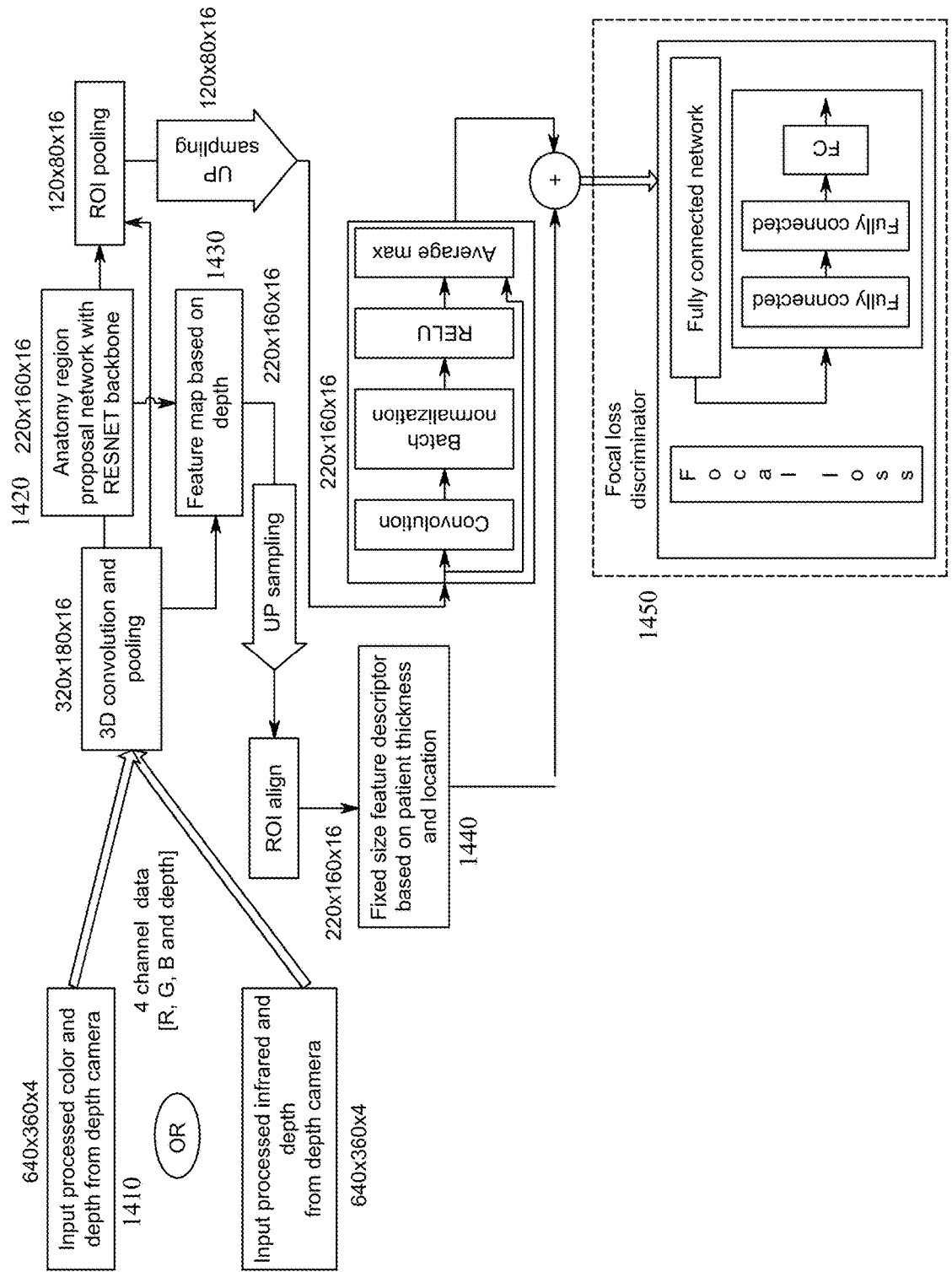
FIG. 14 illustrates a focal loss-based class imbalance object identification network according to aspect of the disclosure.

In accordance with an aspect of the disclosure, FIG. 13 shows AI based identification of the RF coils. As described with reference to FIG. 2, the RF coils may be used for imaging the subject and use of the RF coils (1310) for imaging the subject includes wrapping the RF coils (1310) around the subject body (1320) and imaging the subject. Some non-limiting examples of the imaging coils (1310) include a head coil (1311), a chest coil (1312) and a leg coil (1313). In one aspect of the disclosure, the various RF coils wrapped around the subject body may be identified using a focal loss-based class imbalance object identification network. In accordance with an aspect of the disclosure, FIG. 14 shows a focal loss-based class imbalance object identification network that may be used to identify the RF coils wrapped around the subject body. The focal loss function may be used as a discriminator for identifying the RF coils. According to an exemplary function as shown in FIG. 14, the parameter pt is a notation for the probability of the class labelled with numeric value 1. If the variable y represents the ground-truth value and is either 0 or 1, the probability of $p \in [0, 1]$ is the probability that is estimated by the model for the ground truth or actual class of y=1. To attain some notational ease, the variable pt was defined as:

$$p_t = \begin{cases} p & \text{if } y=1 \\ 1-p & \text{otherwise} \end{cases}$$

The focal loss may be calculated as: $FL(pt)=-(1-pt)^\gamma \log(pt)$.

The modulating factor $(1-pt)^\gamma$ is thus added to the original cross entropy formula. When an instance passed to the model is misclassified and pt is small, the modulating factor is nearly unity and thus does not affect the loss. As pt tends to 1, the modulating factor tends to 0, and again, the loss is not influenced. Thus, all well-classified examples have lower weightage. This down weighting of the various examples can be controlled smoothly by the modulating factor. The AI identified RF coils may be presented to the operator for view along with their orientation.

In accordance with another aspect of the disclosure, FIG. 14 shows the RF coil identification using the AI based deep learning network which may be a class imbalance object identification network that uses focal loss discriminator function. In one example, the input processed color and depth camera images of the subject or the input processed infrared images and depth from the depth camera may be inputted to the AI based deep learning network. The AI network may be configured for automated AI based RF coil, anatomy and its corresponding orientation/view identification which may compute the spatial location, co-ordinates of the identified anatomical area (2D), midpoint of the identified anatomical area (2D), and the 3D coordinates of the anatomy with respect to the subject co-ordinates f(x,y,z), where Z is the thickness of the identified anatomical area.

Once the patient region has been identified and presence of patient is confirmed by 10 (b), the next step may be to identify the coil that is placed or wrapped around the patient's body. In addition to the type, the spatial location of the coil, and depth pattern of the coil may computed using the depth maps (1410). In these depth maps (1410), the feature of coil is extracted and the logical operations that were used to identify the patient is also applied here. The RoI-pooling, region proposal (1420), and depth-based feature extraction (1430) may be employed for processing the input depth map (1410). The additional processing that may be employed is to combine the information from the feature descriptor (1440) of the coils with that of patient thickness, and iteratively sum up the maximum average vector of the rectified linear unit. This iterative summation contains the co-ordinates of the identified coil. This information is fed to focal loss-based discriminator (1450) to remove the spurious and falsely identified coil regions and retain only true coil locations. Once the true co-ordinates, spatial location, and the midpoint of the coil is computed, the next step is to classify the type of the coil, orientation of the patient with coil.

Figure 15:
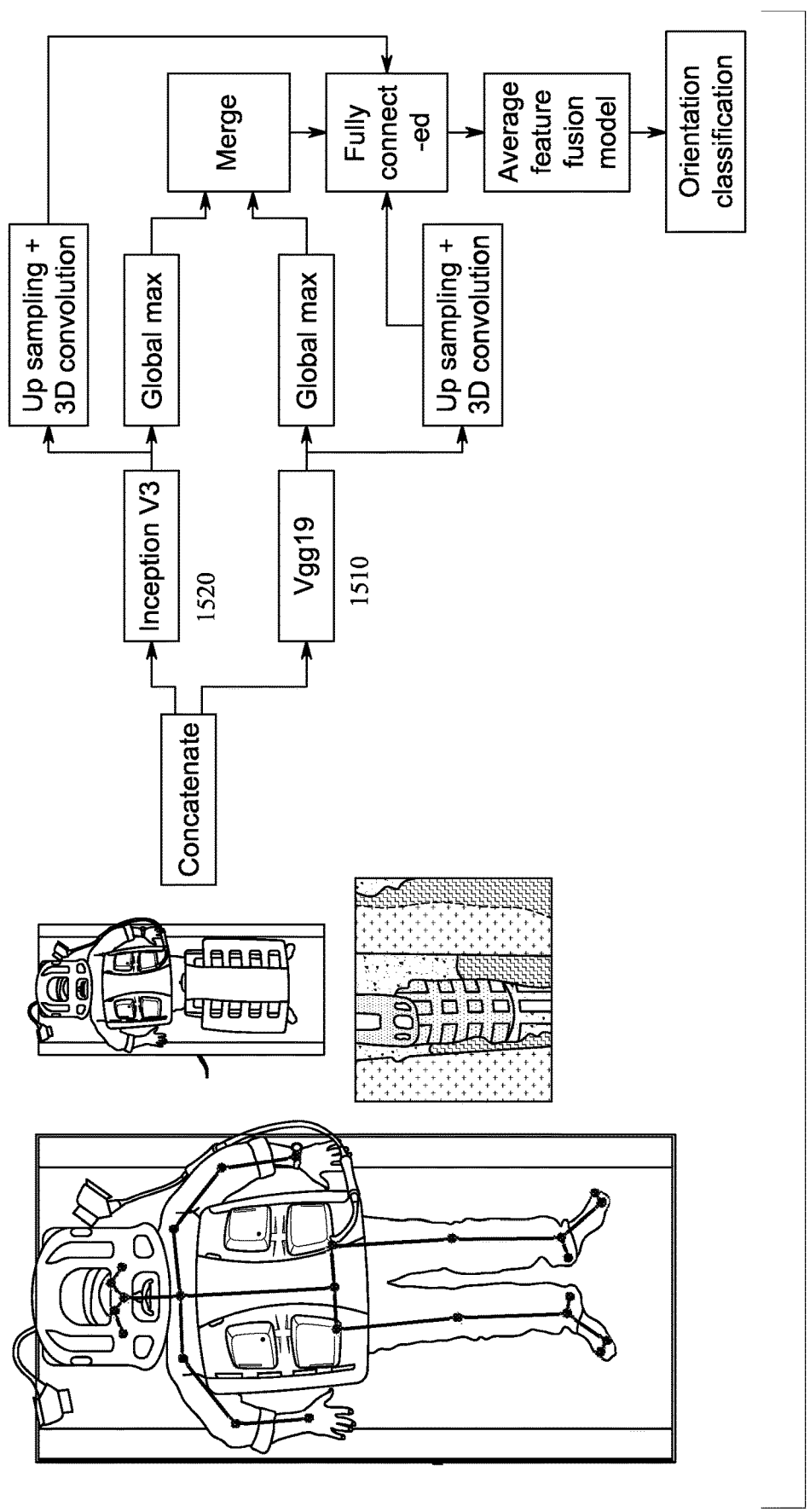
FIG. 15 illustrates an AI based identification of the subject with RF coils according to an aspect of the disclosure.

In accordance with an aspect of the disclosure, FIG. 15 shows AI based identification of the subject wrapped with the RF coils. The AI based identification of the subject with coils may be performed using the methods similar to the method descried with respect to the FIG. 9 and FIG. 10. The images of the subject along with the RF coils obtained using the 3D camera may be inputted to the AI based deep learning module to identify the type of coil and accurate positioning of the RF coils over the subject anatomy. Further, the coil type and orientation of the patient with coil may be classified. The classification categories refer to coil type categories such as head coil, neck, body, extremity coils, and the orientations of the patient such as supine or prone.

This classification of coils may be performed by a vgg 19 neural network (1510). Vgg 19 is a convolutional neural network. The input to cov1 layer is of fixed size RGB image. The image is passed through a stack of convolutional (conv.) layers, where the filters may be used with a very small receptive field: 3×3 (which is the smallest size to capture the notion of left/right, up/down, center). In one of the configurations, it also utilizes 1×1 convolution filter, which may be seen as a linear transformation of the input channels (followed by non-linearity). The convolution stride is fixed to 1 pixel; the spatial padding of convolution layer input is such that the spatial resolution is preserved after convolution Spatial pooling may be carried out by five max-pooling layers, which follow some of the cony. layers (not all the cony. layers are followed by max-pooling). Max-pooling is performed over a 2×2-pixel window, with stride 2. Three Fully Connected (FC) layers follow a stack of convolutional layers: the first two may have 4096 channels each, the third performs 1000-way ILSVRC classification and thus contains 1000 channels (one for each class). The final layer is the soft-max layer. The configuration of the fully connected layers is the same in all networks.

The classification of patient orientation may be performed by another convolutional neural network know as inception v3 (1520). Inception-v3 (1520) is a convolutional neural network that may be forty-eight layers deep. It may contain a suitable algorithm such as RMSProp. that facilitates label smoothing. This a type of regularizing component added to the loss formula that prevents the network from becoming too confident about the orientation of the patient and prevents over fitting. Further, since the patient orientations need to be classified in addition to coils, Factorized Convolutions may be performed to reduce the computational burden as it reduces the number of parameters involved in a network. It also keeps a check on the network efficiency.

Figure 16:
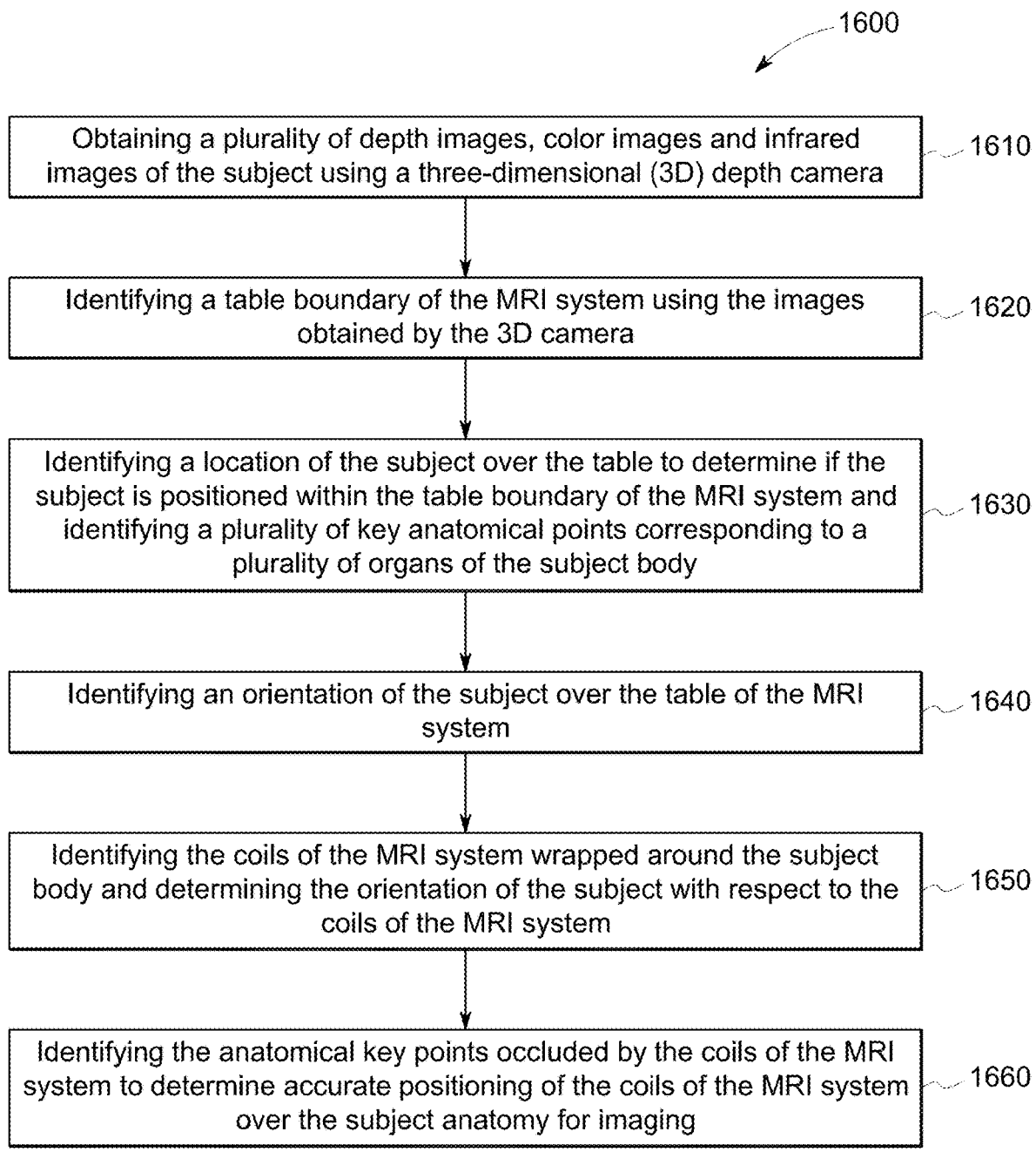
FIG. 16 illustrates a method for automated anatomy and orientation identification of a subject using an artificial intelligence (AI) based deep learning module during occlusion from an imaging coil of a magnetic resonance imaging (MRI) system according to an aspect of the disclosure.

In accordance with an aspect of the disclosure, FIG. 16 shows AI based identification of the anatomy corresponding to the RF coils. Identifying the anatomy corresponding to the RF coil includes identifying the key anatomical points on the subject body corresponding to various organs and anatomical regions of the subject body and connecting the key anatomical points using the grid lines to generate a torso image of the subject body. The key points indicate various organs of the subject body. The 3D camera may be configured to capture the location of the RF coils over the subject body and the AI module may be configured to identify the location of the RF coils over the key points identified by the AI module over the subject body. In accordance with another aspect of the disclosure, the AI module may be configured to identify all the key points located under the RF coil using the key point detection algorithm and verify that the RF coil is suitable for the anatomical region.

Based on the systems and methods described above, in accordance with a further aspect of the disclosure, FIG. 16 shows a method (1600) for automated anatomy and orientation identification of a subject using an artificial intelligence based deep learning module during occlusion from an imaging coil of a magnetic resonance imaging (MRI) system. The method (1600) includes obtaining (1610) a plurality of depth images, color images and infrared images of the subject using a three-dimensional (3D) depth camera. The method (1600) further includes identifying (1620) a table boundary of the MRI system using the images obtained by the 3D camera. The method (1600) further includes identifying (1630) a location of the subject over the table to determine if the subject is positioned within the table boundary of the MRI system and identifying a plurality of key anatomical points corresponding to a plurality of organs of the subject body. The method (1600) further includes identifying (1640) an orientation of the subject over the table of the MRI system. The method (1600) further comprises identifying (1650) the coils of the MRI system wrapped around the subject body and determining the orientation of the subject with respect to the coils of the MRI system. The method (1600) further comprises identifying (1660) the anatomical key points occluded by the coils of the MRI system to determine accurate positioning of the coils of the MRI system over the subject anatomy for imaging. The method (1600) may include identifying all Digital Imaging and Communications in Medicine (DICOM) orientations and anatomical regions of the subject when occluded by hospital gown or blankets. The method further includes identifying all types of RF coils wrapped around the subject when occluded by the hospital gown or blankets.

These and other features of the present disclosure provide an automated AI based detection of the RF coils and its corresponding orientation/view identification from color depth, or infrared and depth frames using the shape and texture of the image. Further, the systems and methods of the disclosure provide an automated AI based RF coil, patient anatomy and its corresponding patient orientation/view identification, which will overlay the anatomy identified area, shape on the color and infrared frames of the patient video thumbnail in the console screen. The systems and methods of the present disclosure provide an automated AI based RF coil, anatomy and its corresponding orientation/view identification under various scanner room illumination conditions such as bright, dark, semi bright, and semi dark conditions. The systems and methods of the present disclosure provide an automated AI based RF coil, anatomy and its corresponding orientation/view identification, which will overlay the orientation identified information as a string on the color and infrared frames of the patient video thumbnail in the console screen, all the anatomies that are seen in the field of view of the camera and may be used to computed the spatial location, co-ordinates of the identified anatomical area (2D), midpoint of the identified anatomical area (2D), and the 3D coordinates of the anatomy with respect to patient co-ordinates f(x, y, z), where Z is the thickness of the identified anatomical area.

This written description uses examples to disclose the invention, including the best mode, and to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for automated anatomy and orientation identification of a subject using an artificial intelligence (AI) based deep learning module, the method comprising:
    positioning a subject over a table of a magnetic resonance imaging (MRI) system and wrapping at least one radiofrequency (RF) imaging coil over the subject;
    obtaining a plurality of depth images, color images and infrared images of the subject using a three-dimensional (3D) depth camera during occlusion of a subject body by the at least one radiofrequency (RF) imaging coil;
    identifying a table boundary of the MRI system using the images obtained by the 3D depth camera;
    identifying a location of the subject in a physical space over the table of the MRI system to determine if the subject is positioned within the table boundary of the MRI system and identifying a plurality of key anatomical points and regions corresponding to a plurality of organs of the subject body;
    identifying an orientation of the subject over the table of the MRI system;
    identifying at least one RF imaging coil type of the MRI system wrapped around the subject body and determining the orientation of the subject with respect to the at least one RF imaging coil of the MRI system; and
    identifying the plurality of key anatomical points and regions occluded by the at least one RF imaging coil of the MRI system to determine accurate positioning of the at least one RF imaging coil of the MRI system over a subject anatomy for imaging and for performing automated landmarking of the subject anatomy.

2. The method of claim 1 wherein obtaining the plurality of images by the 3D depth camera comprises performing a health check of the 3D depth camera for any color model, imaging depth and infrared streaming and calibrating the 3D depth camera for imaging.

3. The method of claim 1 wherein identifying the table boundary of the MRI system comprises:
    changing a 3D camera coordinate system to a patient coordinate system;
    generating a patient physical coordinate system corresponding to the MRI system;
    activating a color, an infrared and a depth stream of the 3D depth camera to generate a color frame, an infrared frame and a depth frame of the subject;
    checking an illumination level of the color frame, noise levels of the depth frame and performing color depth alignment, identification of a blanket in color, infrared and depth frames, decimation filtering, distance thresholding, background subtraction and gaussian smoothening in case the color frame and the depth frames are illuminated and switching to the infrared frame in case of low illumination of the color frames and depth frames to perform gaussian smoothening of the infrared frame to identify the table boundaries of the table of the MRI system.

4. The method of claim 3 further comprises:
    extracting a point cloud data of the table of the MRI system corresponding to the 3D depth camera's coordinate system from the depth frames of the 3D camera;
    obtaining an original point cloud of the table of the MRI system;
    extracting the point cloud data in a first plane, a floor plane and from the rest of the
    point cloud data;
    obtaining the point cloud data without the floor plane;
    extracting the point cloud data in a second plane, the table plane of the MRI system and from the remaining point cloud data; and
    computing four corners and midpoint of the table of the MRI system using the second plane;
    wherein if a depth image is noisy and the 3D depth camera is unable to extract the point cloud data, the AI based deep learning module identifies the table boundary and outputs the four corners of the table boundary using a shape detection neural network.

5. The method of claim 1 wherein identifying the location of the subject over the table of the MRI system to determine if the subject is positioned within the table boundary of the MRI system comprises processing the images obtained by the 3D depth camera by the AI based deep learning module to identify the MRI table boundary and identifying if the subject is located within the MRI table boundary.

6. The method of claim 1 wherein identifying the plurality of key anatomical points corresponding to the plurality of organs of the subject body comprises identifying a plurality of organs on the subject body, marking the organs with a points and joining the points by a plurality of grid lines to generate a torso image of the subject for automated landmarking, and identifying the plurality of key anatomical points and the orientation of the subject further comprises identifying the regions occluded by the blanket, a hospital gown and a cover to determine accurate positioning of the at least one RF imaging coil of the MRI system over the subject anatomy for imaging.

7. The method of claim 6 wherein identifying the plurality of key anatomical points corresponding to the plurality of organs of the subject body is carried out before wrapping the at least one RF imaging coil around the subject body using the AI based deep learning module.

8. The method of claim 1 wherein identifying the orientation of the subject over the table of the MRI system comprises processing the images obtained by the 3D depth camera by the AI based deep learning module to identify a direction or the orientation in which the subject has lied down on the MRI table.

9. The method of claim 1 wherein identifying the at least one RF imaging coil type of the MRI system wrapped around the subject body comprises employing a focal loss-based class imbalance object identification network to identify the type of the at least one RF imaging coil wrapped around the subject body with and without hospital gown and blankets.

10. The method of claim 1 wherein identifying the anatomical key points or regions occluded by the at least one RF imaging coil of the MRI system comprises identifying the anatomical regions occluded by the type of the at least one RF imaging coil of the MRI system and identifying using the AI based deep learning module if the at least one RF imaging coil is accurately placed over the respective subject organ according to an imaging protocol preloaded on the AI based deep learning module.

11. The method of claim 10 wherein identifying the accurate placement of the at least one RF imaging coils over the subject organ comprises:
identifying the at least one RF imaging coil of the MRI system wrapped around the subject body;
identifying the at least one RF imaging coil wrapped around the subject body that is occluded by a blanket;
identifying the anatomies selected by an operator that correspond to the at least one wrapped RF imaging coil of the MRI system;
identifying the anatomies selected by an operator that correspond to the at least one wrapped RF imaging coil of the MRI system and occluded by the blanket; and
comparing using the AI based deep learning module, the identified anatomies corresponding to the at least one RF imaging coils of the MRI system with the operator selected anatomy.

12. The method of claim 11 further comprising alerting the operator of the MRI system if the anatomies identified by the AI based deep learning module do not match with the anatomies selected by the operator.

13. The method of claim 11 further comprising carrying out MR imaging if the anatomies identified by the AI based deep learning module match with the anatomies selected by the operator.

14. The method of claim 1 further comprising:
inputting an operator selected imaging protocol through an operator console and preloading the imaging protocol on to the AI based deep learning module;
obtaining the subject images using the 3D depth camera and inputting the subject images to the AI based deep learning module;
comparing using the AI based deep learning module the images obtained by the 3D depth camera with the operator selected protocol to determine if the subject position and the orientation matches the imaging protocol;
obtaining a landmark position with respect to the identified anatomy and the at least one RF imaging coil position and
alerting the operator to change the subject position and the coil settings until the subject position and orientation matches the imaging protocol preloaded on to the AI based deep learning module.

15. The method of claim 1 further comprising automatically identifying the appropriate imaging protocol based on the at least one identified imaging RF imaging coils of the MRI system and underlying anatomy of the subject using the AI based deep learning module.

16. The method of claim 1 further comprising automatically populating a list of the at least one RF imaging coil of the MRI system, anatomies, and corresponding anatomy mid-point for automated land marking seen inside the MR table boundary.

17. A system for an automated anatomy and orientation identification of a subject using an artificial intelligence (AI) based deep learning module during occlusion from at least one RF imaging coil of a magnetic resonance imaging (MRI) system, the system comprising:
a three-dimensional (3D) depth camera configured to capture a plurality of depth images, color images and infrared images of the subject positioned on a table of the magnetic resonance imaging (MRI) system;
a computer system connected to the 3D depth camera and configured to receive the images from the 3D depth camera, wherein the computer system comprises:
a processor;
a memory connected to the processor;
at least one artificial intelligence (AI) based deep learning module deployed over the memory, wherein the AI based deep learning module is configured to:
identify a table boundary of the MRI system using the images obtained by the 3D camera;
identify a physical location of the subject over the table to determine if the subject is positioned within the table boundary of the MRI system and identify a plurality of key anatomical points corresponding to a plurality of organs of a subject body;
identify a plurality of Digital Imaging and Communications in Medicine (DICOM) orientations of the subject over the table of the MRI system;
identify the at least one RF imaging coil wrapped around the subject body and determine the orientation of the subject with respect to the at least one RF imaging coil; and
identify the plurality of key anatomical points occluded by the at least one RF imaging coil to determine an accurate position of the at least one RF imaging coil over a subject anatomy for imaging.

18. The system of claim 17 wherein the 3D depth camera may be ceiling mounted, wall mounted, stand mounted, scanner mounted or lateral mounted.

19. The system of claim 17 wherein the orientation of the subject comprises head-first,
feet first, supine, prone, left decubitus, right decubitus, and other DICOM positions.

20. The system of claim 17 wherein the at least one RF coil of the MRI system comprises radiofrequency (RF) head coil, chest coil, leg coil, full body coil, extremity coils, abdomen coil, and MRI volume coil.

21. The system of claim 17 wherein the computer system is configured to generate an alert if a mismatch is detected between an imaging protocol recommended by the AI based deep learning module and a plurality of imaging parameters set by the operator and identified by the 3D depth camera frames.

22. The system of claim 21 wherein the imaging parameters include coil type, subject orientation, subject anatomy and subject location over the table of the MRI system.

23. The system of claim 22 wherein position of the subject anatomy with the at least one identified RF imaging coil is used for auto land marking.

* * * * *